(12) United States Patent
Eveleth et al.

(10) Patent No.: US 10,537,607 B2
(45) Date of Patent: Jan. 21, 2020

(54) TREATMENT OF AUTOIMMUNE AND/OR INFLAMMATORY DISEASE USING NOVEL CAVEOLIN MODULATORS

(71) Applicant: E&B TECHNOLOGIES LLC, San Diego, CA (US)

(72) Inventors: David Eveleth, San Diego, CA (US); William C. Sessa, Madison, CT (US)

(73) Assignee: E&B Technologies LLC, San Diego, CA (US)

(*) Notice: Subject to any disclaimer, the term of this patent is extended or adjusted under 35 U.S.C. 154(b) by 0 days.

(21) Appl. No.: 15/039,826

(22) PCT Filed: Nov. 21, 2014

(86) PCT No.: PCT/US2014/066940
§ 371 (c)(1),
(2) Date: May 26, 2016

(87) PCT Pub. No.: WO2015/080980
PCT Pub. Date: Jun. 4, 2015

(65) Prior Publication Data
US 2017/0128520 A1    May 11, 2017

Related U.S. Application Data

(60) Provisional application No. 61/909,005, filed on Nov. 26, 2013.

(51) Int. Cl.
*A61K 38/08* (2019.01)
*A61K 38/17* (2006.01)

(52) U.S. Cl.
CPC .......... *A61K 38/08* (2013.01); *A61K 38/1709* (2013.01)

(58) Field of Classification Search
None
See application file for complete search history.

(56) References Cited

U.S. PATENT DOCUMENTS

| 8,420,096 B2* | 4/2013 | Hawiger ............ C07K 14/4703 424/184.1 |
| 2005/0181474 A1 | 8/2005 | Giordano et al. |
| 2006/0123511 A1 | 6/2006 | Conner et al. |
| 2009/0209458 A1 | 8/2009 | Hawiger et al. |
| 2009/0226372 A1* | 9/2009 | Ruoslahti ......... A61K 47/48238 424/9.1 |
| 2012/0149651 A1 | 6/2012 | Sessa |

FOREIGN PATENT DOCUMENTS

| JP | 2005-503321 A | 2/2005 |
| JP | 2011-514160 A | 5/2011 |
| WO | 2002-020768 A2 | 3/2002 |
| WO | WO 02/20768 * | 3/2002 |
| WO | 2008-046228 A1 | 4/2008 |
| WO | 2009-143864 A1 | 12/2009 |

OTHER PUBLICATIONS

Teesalu et al. (Proc Natl Acad Sci U S A. Sep. 22, 2009;106(38):16157-62).*
Kim et al. (J Korean Med Sci 2002; 17: 389-94).*
Written Opinion of the International Searching Authority and International Search Report for related International Application No. PCT/US2014/066940 in 17 pages.
European Search Report dated May 9, 2017, issued for European Application No. EP14865347, 7 pages.
Notice of Reasons for Rejection for Japanese application No. 2016-554817 dated Jul. 31, 2018 in 6 pages.

* cited by examiner

*Primary Examiner* — Sergio Coffa
(74) *Attorney, Agent, or Firm* — Procopio, Cory, Hargreaves & Savitch LLP

(57) ABSTRACT

Provided herein are novel compositions, specifically, caveolin modulators, and methods to treat and/or prevent autoimmune and/or inflammatory diseases/conditions using such compositions.

6 Claims, 8 Drawing Sheets

Specification includes a Sequence Listing.

US 10,537,607 B2

TREATMENT OF AUTOIMMUNE AND/OR INFLAMMATORY DISEASE USING NOVEL CAVEOLIN MODULATORS

RELATED APPLICATIONS

This application claims the benefit of the priority of U.S. provisional application No. 61/909,005, filed Nov. 26, 2013.

FIELD OF THE INVENTION

The instant disclosure relates to novel compositions and methods to treat and/or prevent autoimmune and/or inflammatory diseases/conditions using such compositions.

BACKGROUND OF THE INVENTION

The causative mechanism of many diseases is the overactivity of a biological pathway. A peptide that can reduce the activity of the biological pathway can be effective in the prophylaxis and/or treatment of the disease caused by the over activity of the biological pathway. Similarly the causative mechanism of many diseases is the over production of a biological molecule. A peptide that can reduce the production of the biological molecule or block the activity of the over produced biological molecule can be effective in the prophylaxis and/or treatment of the disease caused by the over production of the biological molecule.

Conversely, the causative mechanism of many diseases is the under activity of a biological pathway. A peptide that can increase the activity of the biological pathway can be effective in the prophylaxis and/or treatment of the disease caused by the under activity of the biological pathway. Similarly, the causative mechanism of many diseases is the under production of a biological molecule. A peptide that can increase the production of the biological molecule or mimic the biological activity of the under produced biological molecule can be effective in the prophylaxis and/or treatment of the disease caused by the under production of the biological molecule.

Caveolins are cholesterol binding proteins that can potentially regulate a variety of signal transduction pathways (Smart et al., (1999) *Mol. Cell. Biol.* 19, 7289-7304; Kurzchalia & Parton, (1999) *Curr. Opin. Cell. Biol.* 11, 424-431). For example, numerous researchers have demonstrated localization of proteins in caveolae, interaction of these proteins with caveolins, and the ability of overexpressed caveolins or peptides derived from caveolins to suppress or stimulate signaling functions in vitro or in cultured cells (Li et al., (1996) *J. Biol. Chem.* 271, 29182-29190; Razani et al., (1999) *J. Biol. Chem.* 274, 26353-26360; Nasu et al., (1998) *Nat. Med.* 4, 1062-1064; Garcia-Cardena et al., (1997) *J. Biol. Chem.* 272, 25437-25440). However, the importance of caveolins as modulators of signal transduction in vivo is controversial since caveolins-1 and -3, per se, are cholesterol binding proteins that deliver cholesterol from the endoplasmic reticulum to the plasmalemma thereby regulating signal transduction indirectly by modulating the cholesterol content of lipid raft domains and caveolae (Roy et al., (1999) *Nat. Cell Biol.* 1, 98-105; Sternberg et al., (1999) *Nat. Cell Biol.* 1, E35-37).

Studies have focused on the subcellular trafficking and regulation of endothelial nitric oxide synthase (eNOS). eNOS derived NO is necessary for the maintenance of systemic blood pressure, vascular remodeling, angiogenesis and wound healing (Huang et al., (1995) *Nature* 377, 239-242; Murohara et al., (1998) *J. Clin. Invest.* 101, 2567-0.2578; Rudic et al., (1998) *J. Clin. Invest.* 101, 731-736; Lee et al., (1999) *Am. J. Physiol.* 277, H1600-1608). eNOS is a dually acylated, peripheral membrane protein that targets to lipid raft domains and caveolae (Garcia-Cardena et al., (1996) *Proc. Natl. Acad. Sci. USA* 93, 6448-6453; Liu et al., (1997) *J. Cell Biol.* 137, 1525-1535). In caveolae, eNOS can physically interact with caveolins-1 and -3 by binding to their putative scaffolding domain located between amino acids 82-101 (Li et al., (1996) *J. Biol. Chem.* 271, 29182-29190) and this interaction, renders eNOS in its "less active" state (Garcia-Cardena et al., (1997) *J. Biol. Chem.* 272, 25437-25440; Ju et al., (1997) *J. Biol. Chem.* 272, 18522-18525; Michel et al., (1997) *J. Biol. Chem.* 272, 25907-25912). The data for this model was largely elucidated in vitro using overexpression systems, fusion proteins or yeast-two hybrid screening to map the interacting domains.

In support of caveolin as a negative regulator of eNOS are studies showing that peptides derived from the scaffolding domain of caveolin-1 will disrupt the binding of eNOS to caveolin and dose-dependently inhibit NOS activity in vitro ($IC_{50}$=1-3 µM) by slowing electron flux from the reductase to the oxygenase domain of NOS (Garcia-Cardena et al., (1997) *J. Biol. Chem.* 272, 25437-25440; Ju et al., (1997) *J. Biol. Chem.* 272, 18522-18525; Ghosh et al., (1998) *J. Biol. Chem.* 273, 22267-22271).

Treatment of one or more cells with a peptide comprising at least one caveolin scaffolding domain has resulted in the reduction and/or elimination of one or more conditions or afflictions of the treated tissue, organ or organism. For example, treatment with a peptide comprising at least one caveolin scaffolding domain has been shown to reduce or eliminate inflammation and tumor cell angiogenesis and proliferation. (See U.S. Pat. No. 8,349,798, which is incorporated herein by reference.)

Multiple sclerosis (MS) and neuromyelitis optica (NMO) are diseases of the central nervous system (CNS) that damage the myelin sheath surrounding the nerve cells, leading to visual disturbances, muscle weakness, loss of coordination, numbness, and reduced mental function, among other symptoms. While the causes of these diseases are uncertain, some believe them to be autoimmune disorders. Uveitis is inflammation of the uvea, the middle layer of the eye, which is known to occur in some autoimmune diseases such as rheumatoid arthritis and ankylosing spondylitis. Symptoms may include eye pain, blurring of vision, light sensitivity and decreased vision. There are no known cures for these debilitating diseases and other autoimmune disorders—treatment is primarily palliative, and in many cases, minimally effective in allowing disease sufferers to maintain a reasonable quality of life.

Accordingly, the need exists for new approaches for the prophylaxis and/or treatment of autoimmune diseases and inflammatory diseases. The present invention is directed to such a need.

SUMMARY OF THE INVENTION

In one aspect of the invention, a method is provided for treating an inflammatory disease or condition in a subject comprising administering a composition comprising an isolated transport peptide comprising the amino acid sequence RRPPR (SEQ ID NO. 1). In specific embodiments, the inflammatory disease or condition is uveitis, multiple sclerosis, neuromyelitis optica, traumatic brain injury or inflammatory bowel disease.

In some embodiments, the transport peptide consists of SEQ ID NO. 1. In some embodiments, the transport peptide selectively binds to a target cell or crosses a cell membrane. In specific embodiments, the target cell comprises an endothelial cell, a cardiac cell, a skeletal muscle cell or a brain cell. In various embodiments, the composition further comprises a pharmaceutically acceptable carrier.

In some embodiments, the composition comprises a transport construct, wherein the transport construct comprises a cargo moiety linked to the transport peptide comprising SEQ ID NO. 1. In specific embodiments, the cargo moiety is selected from the group consisting of a nucleic acid; a peptide; a protein; an oligosaccharide; a lipid; a glycolipid; a lipoprotein; a small molecule compound; a therapeutic drug; an UV-vis, fluorescent or radioactive label; an imaging agent; a diagnostic agent; a prophylactic agent; a liposome and a virus.

In various embodiments, the cargo moiety is covalently linked to the transport peptide through a linker or a chemical bond. In some embodiments, the transport construct selectively binds to a target cell or crosses a cell membrane. In specific embodiments, the target cell comprises an endothelial cell, a cardiac cell, a skeletal muscle cell or a brain cell.

In some embodiments the cargo moiety is at least one selected from the group consisting of SEQ ID NOS. 3-6. In specific embodiments, the transport construct comprises at least one sequence selected from the group consisting of: SEQ ID NO.1/SEQ ID NO.3; SEQ ID NO.1/SEQ ID NO.4; SEQ ID NO.1/SEQ ID NO.5; SEQ ID NO.1/SEQ ID NO.6; SEQ ID NO.3/SEQ ID NO.1; SEQ ID NO.4/SEQ ID NO.1; SEQ ID NO.5/SEQ ID NO.1; and SEQ ID NO.6/SEQ ID NO. 1.

In various embodiments, the composition comprises a nucleic acid encoding a transport peptide comprising SEQ ID NO. 1. In specific embodiments, the nucleic acid comprises 5'-CGGCGCCCGCCTCGT-3' (SEQ ID NO. 7).

In some embodiments, the composition further comprises an isolated nucleic acid encoding at least one cargo moiety. In specific embodiments, the cargo moiety is selected from the group consisting of: a peptide; a protein; a biologically active compound; a label; an imaging agent; a diagnostic agent; a therapeutic agent; and a prophylactic agent. In some embodiments, the cargo moiety is selected from the group consisting of SEQ ID NOS. 3-6.

In some embodiments, the isolated nucleic acid encodes the transport peptide. In specific embodiments, the composition further comprises transcriptional activation elements that allow for the expression of the nucleic acid encoding the transport peptide.

In some embodiments, the composition comprises a nucleic acid encoding a cargo moiety in-frame with the nucleic acid encoding the transport peptide.

In some embodiments, the composition comprises an isolated host cell comprising exogenous nucleic acid encoding a transport peptide comprising the amino acid sequence SEQ ID NO. 1. In specific embodiments, the nucleic acid is a vector comprising (a) a nucleic acid encoding the transport peptide, and (b) a nucleic acid encoding a cargo moiety in-frame with the nucleic acid encoding the transport peptide. In various embodiments the composition further comprises transcriptional activation elements Also provided herein are methods for treating a subject in need by delivering a cargo moiety to or into a target cell, the method comprising contacting the target cell with a transport construct, wherein the transport construct comprises a cargo moiety and a transport peptide comprising the amino acid sequence SEQ ID NO. 1, whereby the cargo moiety is delivered to or into the target cell. In specific embodiments, the cargo moiety is covalently linked to the transport peptide through a linker or a chemical bond. In some embodiments, the cargo moiety is at least one selected from the group consisting of a nucleic acid; a peptide; a protein; an oligosaccharide; a lipid; a glycolipid; a lipoprotein; a small molecule compound; a therapeutic drug; an UV-vis, fluorescent or radioactive label; an imaging agent; a diagnostic agent; a prophylactic agent; a liposome and a virus. In various embodiments, the target cell comprises an endothelial cell, a cardiac cell, a skeletal muscle cell or a brain cell.

Provided herein are methods for delivering a cargo moiety to or into a target cell of a subject in need thereof, the method comprising administering to the subject a therapeutically effective amount of a pharmaceutically acceptable composition comprising a transport construct, wherein the transport construct comprises the cargo moiety and a transport peptide comprising the amino acid sequence SEQ ID NO. 1, whereby the cargo moiety is delivered to or into the target cell of the subject. In specific embodiments, the cargo moiety is covalently linked to the transport peptide through a linker or a chemical bond. In various embodiments, the cargo moiety is at least one selected from the group consisting of a nucleic acid; a peptide; a protein; an oligosaccharide; a lipid; a glycolipid; a lipoprotein; a small molecule compound; a therapeutic drug; an UV-vis, fluorescent or radioactive label; an imaging agent; a diagnostic agent; a prophylactic agent; a liposome and a virus. In some embodiments, the target cell comprises an endothelial cell, a cardiac cell, a skeletal muscle cell or a brain cell.

As described herein, in various embodiments the compositions are administered by at least one route selected from the group consisting of intravenous, oral, inhalational, rectal, vaginal, transdermal, intranasal, buccal, sublingual, parenteral, intrathecal, intragastrical, ophthalmic, pulmonary and topical. In some embodiments the subject is a mammal. In specific embodiments the mammal is a human.

*P<0.05 compared with vehicle, and †P<0.05 compared with AP-Cav+VEGF, n=4 in duplicate.

Figure 2A:
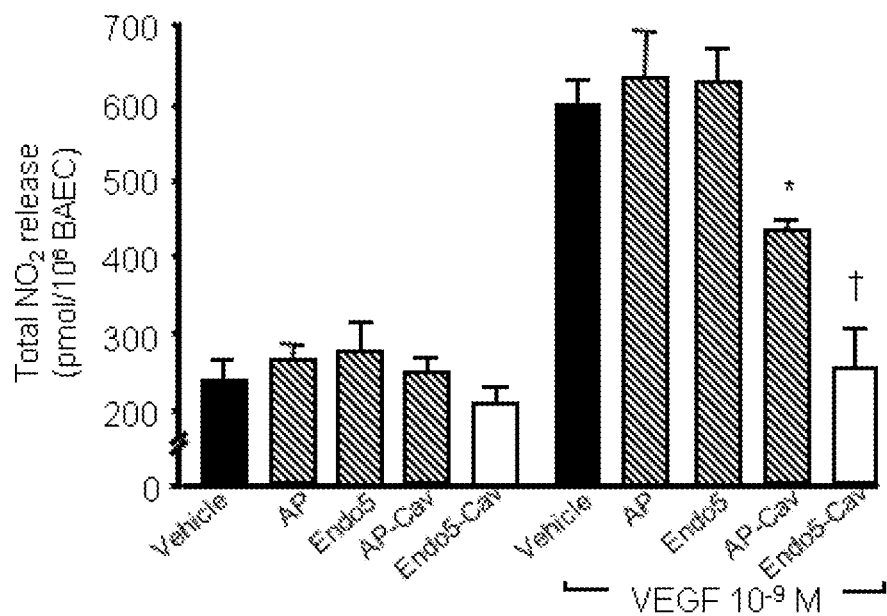
FIG. 2A is a bar graph demonstrating that when cultured bovine aorta endothelial cells (BAEC) were pretreated for 6 hours with the indicated peptides ($10^{-5}$ M) and stimulated with VEGF ($10^{-9}$ M) for 30 minutes as indicated, Endo5-Cav (SEQ ID NO. 1/SEQ ID NO. 5) completely blocked VEGF-induced NO release. *$P<0.05$ compared with vehicle, and †$P<0.05$ compared with AP-Cav+VEGF, n=4 in triplicate.
Figure 2B:
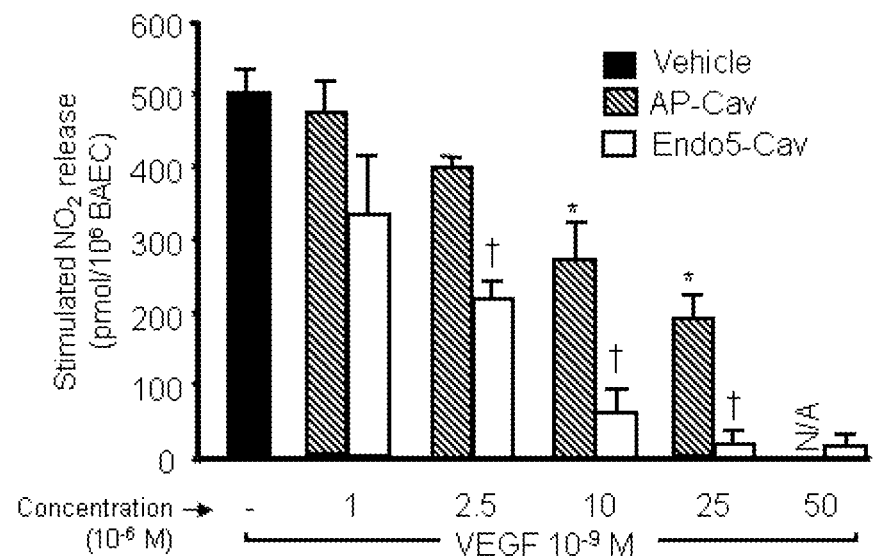
FIG. 2B is a bar graph demonstrating that when cultured BAEC were pretreated with peptides ($1\text{-}50\times10^{-6}$ M) for 6 hours and stimulated with VEGF as described above, AP-Cav (SEQ ID NO. 2/SEQ ID NO. 5) and Endo5-Cav (SEQ ID NO. 1/SEQ ID NO. 5) showed a dose-dependent effect. *$P<0.05$ compared with vehicle, and †$P<0.05$ compared with AP-Cav+VEGF, n=4 in duplicate.
Figure 2C:
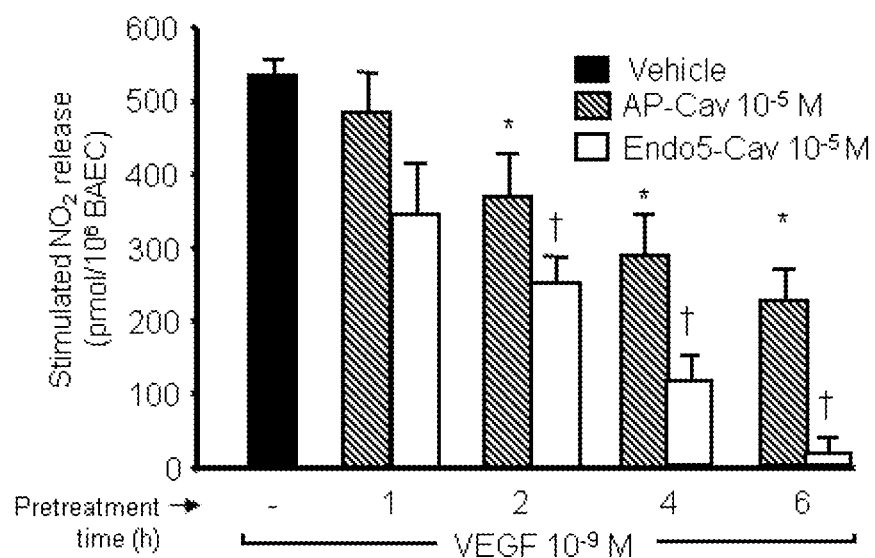
FIG. 2C is a bar graph demonstrating that when BAEC were treated with peptides ($10^{-5}$ M) for 1, 2, 4 or 6 hours, and stimulated with VEGF as described above, AP-Cav (SEQ ID NO. 2/SEQ ID NO. 5) and Endo5-Cav (SEQ ID NO. 1/SEQ ID NO. 5) showed time dependent effects.
Figure 2D:
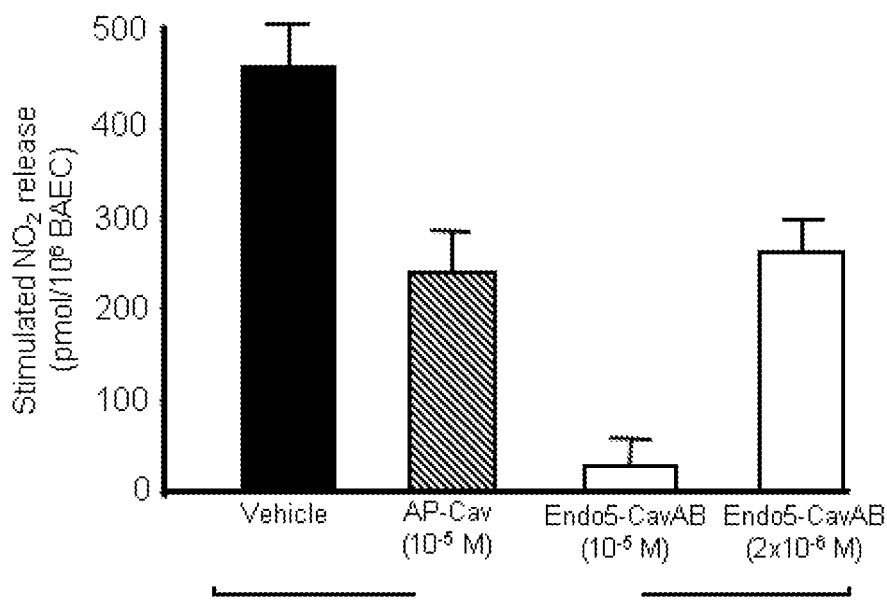
FIG. 2 is a series of bar graphs showing the finding that Endo5-Cav (SEQ ID NO. 1/SEQ ID NO. 5) is more potent than AP-Cav (SEQ ID NO. 2/SEQ ID NO. 5) at blocking VEGF-induced NO release.

FIG. 2D is a bar graph demonstrating that substitution of AP (SEQ ID NO. 2) to Endo5 (SEQ ID NO. 1) and shortening of Cav(82-101) (SEQ ID NO. 5) to CavAB(82-95)(SEQ ID NO. 6) (Endo5-CavAB; $10^{-5}$ M) completely blocked VEGF-induced NO release, whereas Endo5-CavAB (SEQ ID NO. 1/SEQ ID NO. 6)($2\times10^{-6}$ M), a much shorter peptide at a lesser dose, had a similar effect to AP-Cav (SEQ ID NO. 2/SEQ ID NO. 6)($10^{-5}$ M). This figure illustrates the enhanced potency of Endo5-CavAB (SEQ ID NO. 1/SEQ ID NO. 6). In this example, bovine aortic endothelial cells were exposed to peptides for 6 hrs followed by stimulation with VEGF for 30 min. Nitrite levels in the cell supernatant were determined using a Sievers NO chemiluminescence analyzer.

Figure 3A:
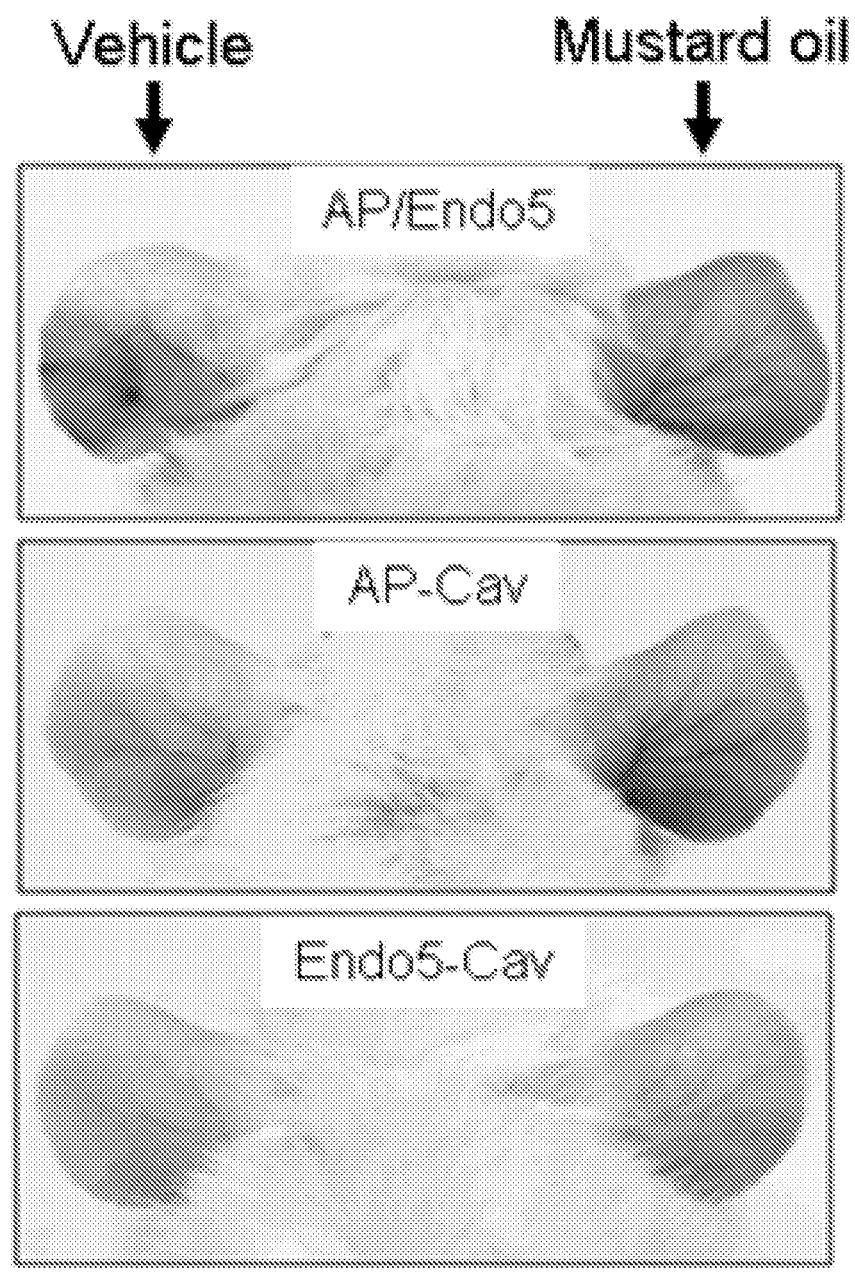

FIG. 3A illustrates that pretreatment of mice with AP-Cav (SEQ ID NO. 2/SEQ ID NO. 5) (1 mg/kg) or the same molar dose of Endo5-Cav (SEQ ID NO. 1/SEQ ID NO. 5) for 1 hour prevented mustard oil-induced increase in vascular permeability (right ear; 30 minutes), whereas control peptides had no significant effect. In this example, left ears were painted with mineral oil alone (vehicle, baseline control) and mice were pre-injected with Evans blue. *P<0.05 compared with control peptide, and †P<0.05 compared with AP-Cav+ mustard oil. n=6 or 8 per group in duplicate.

Figure 3B:
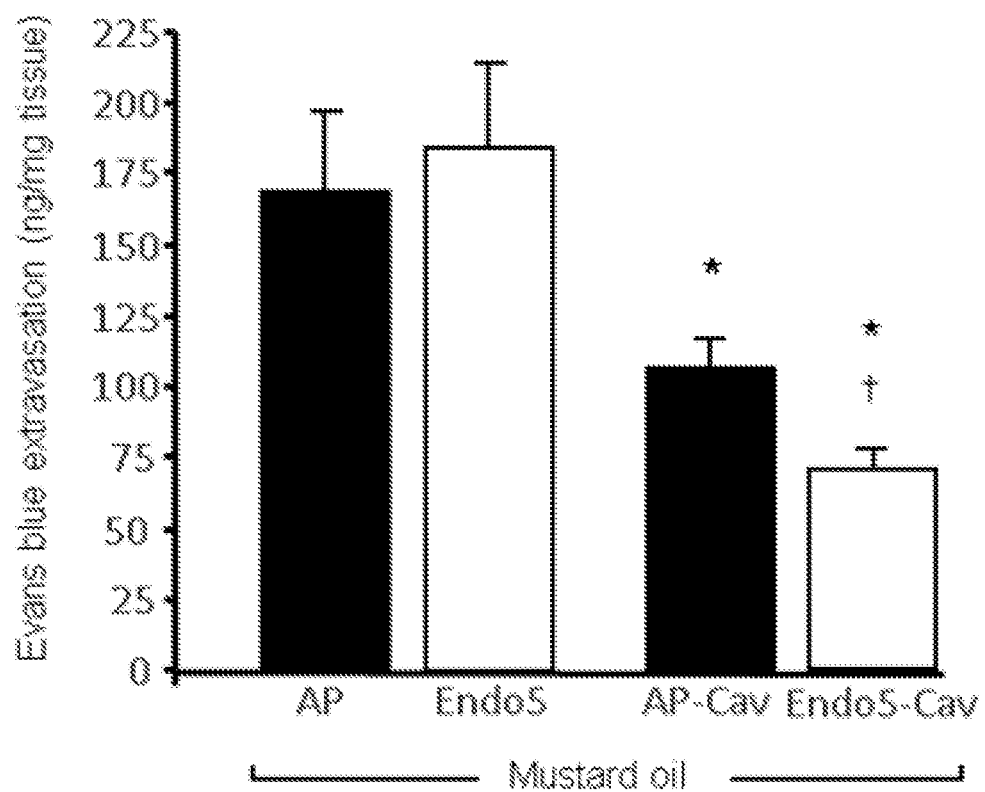

FIG. 3B provides representative values for the data in FIG. 3A.

Figure 4A:
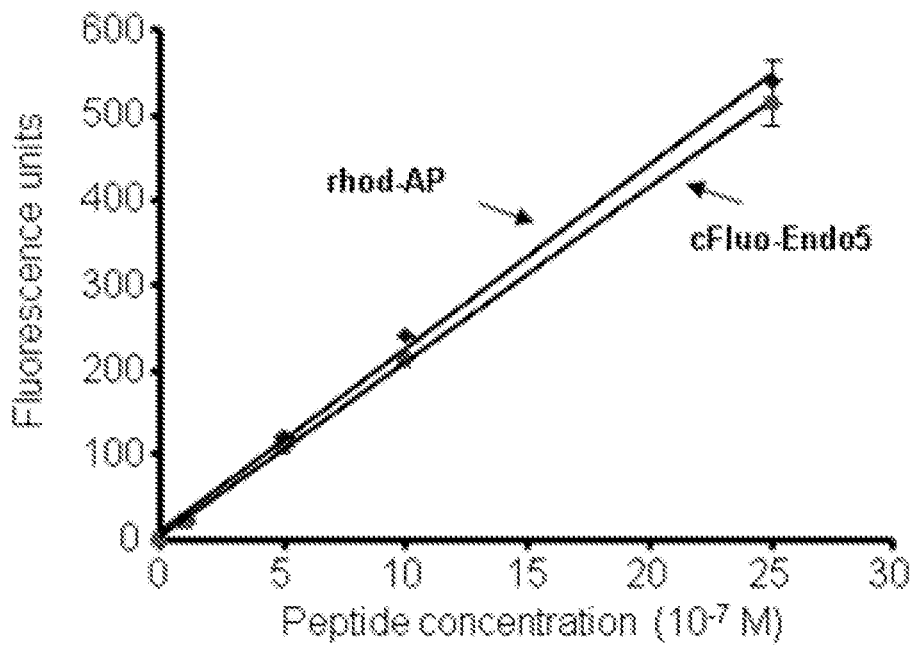

FIG. 4A is a graph showing linearity between peptide concentration in solution and fluorescence values. In this example, fluorescence readouts for similar concentration of rhodamine-AP (rhod-AP) and carboxyfluorescein-Endo5 (cFluo-Endo5) dissolved in the same cell lysis solution used in FIG. 4B were performed. Peptides were used separately to prevent interference.

Figure 4B:
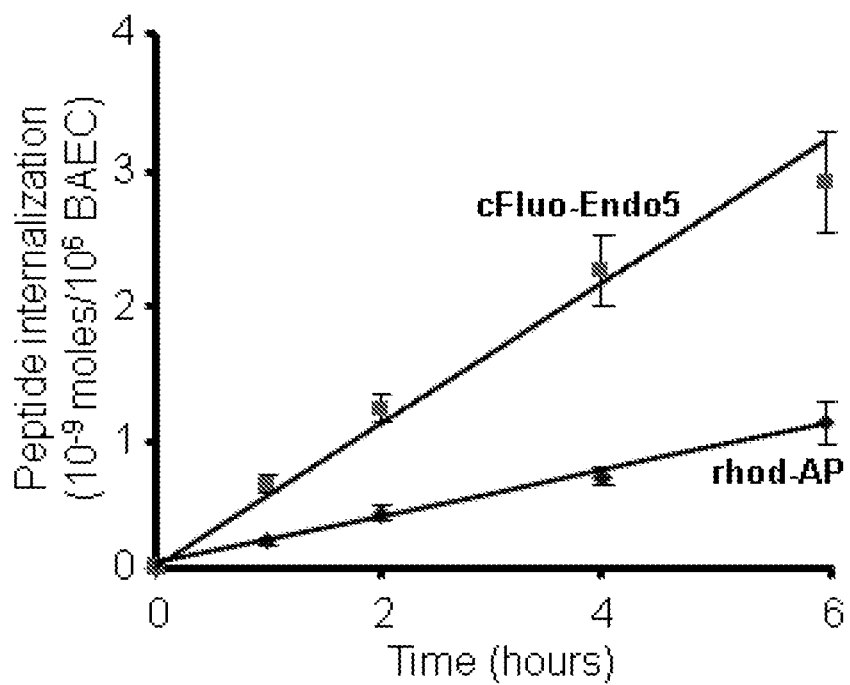

FIG. 4B is a graph showing that the carboxyfluorescein-Endo5 rate of internalization is greater than that of rhodamine-AP. In this example, cultured bovine aorta endothelial cells were incubated for 1, 2, 4 or 6 hours with individual peptides, acid washed, rinsed, trypsinized, lysed and total internal fluorescence was determined and converted to moles of peptides per $10^6$ by using a standard curve. Cells incubated with peptides for 5 min and treated as described were used as background for non-internalized staining.

Figure 5A:
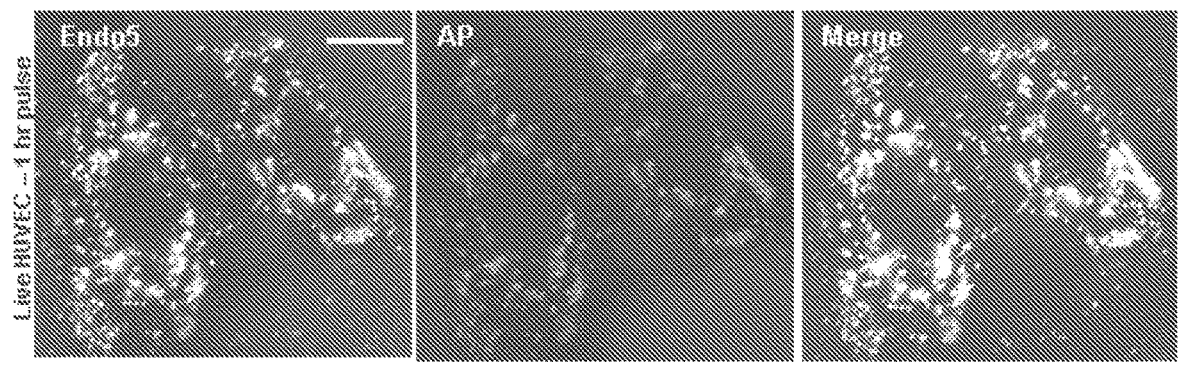

FIG. 5A illustrates the live imaging using an epifluorescence microscope of unfixed cultured human umbilical vein endothelial cells (HUVEC) that were treated with carboxyfluorescein-Endo5 (left) or rhodamine-AP (center; $10^{-5}$ M) for 1 hour (pulse) and rinsed. Note the punctate staining with both peptides and the absence of nuclear staining (oval-shaped dark zone). Merged images showed localization (right) between both peptides.

Figure 5B:
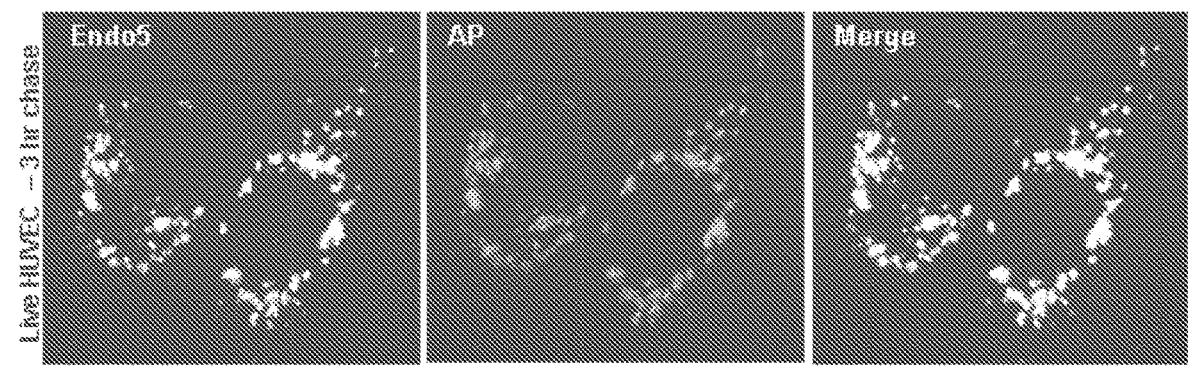

FIG. 5B illustrates co-localization (right) between both peptides was still visualized in the live imaging after peptide localization was chased for two hours in live human umbilical vein endothelial cells (HUVEC).

Figure 5C:
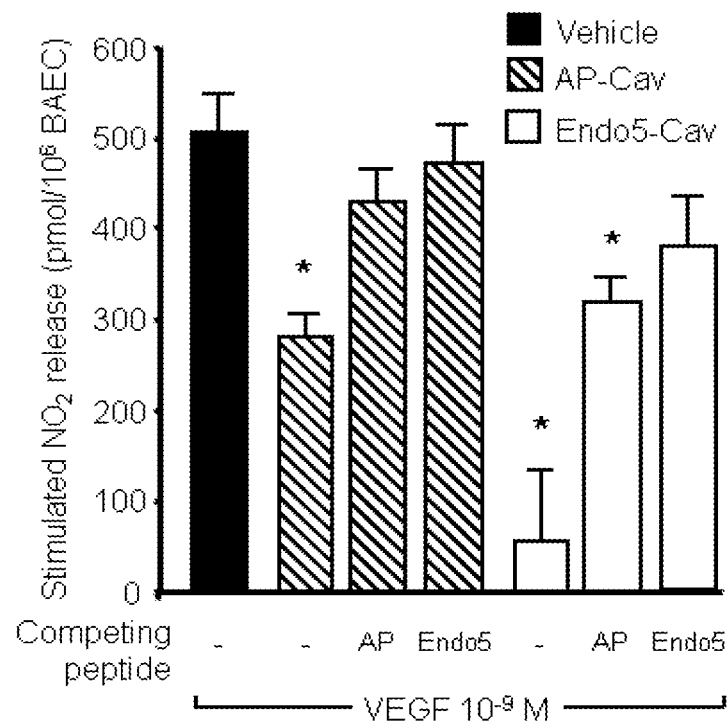

FIG. 5C illustrates that when cultured bovine aorta endothelial cells were pretreated with either AP (SEQ ID NO. 2) or Endo5 (SEQ ID NO. 1) (bot at $5\times10^{-5}$ M) and incubated for 6 h with either AP-Cav (SEQ ID NO. 2/SEQ ID NO. 5) or Endo5-Cav (SEQ ID NO. 1/SEQ ID NO. 5) (both at $10^{-5}$ M) and stimulated with VEGF ($10^{-9}$ M) as described illustrated by FIGS. 2A-2D, Endo5 and AP prevented AP-Cav and Endo5-Cav inhibition of VEGF-induced NO release. *P<0.05 compared with vehicle, n=6 per group in triplicate.

Figure 6:
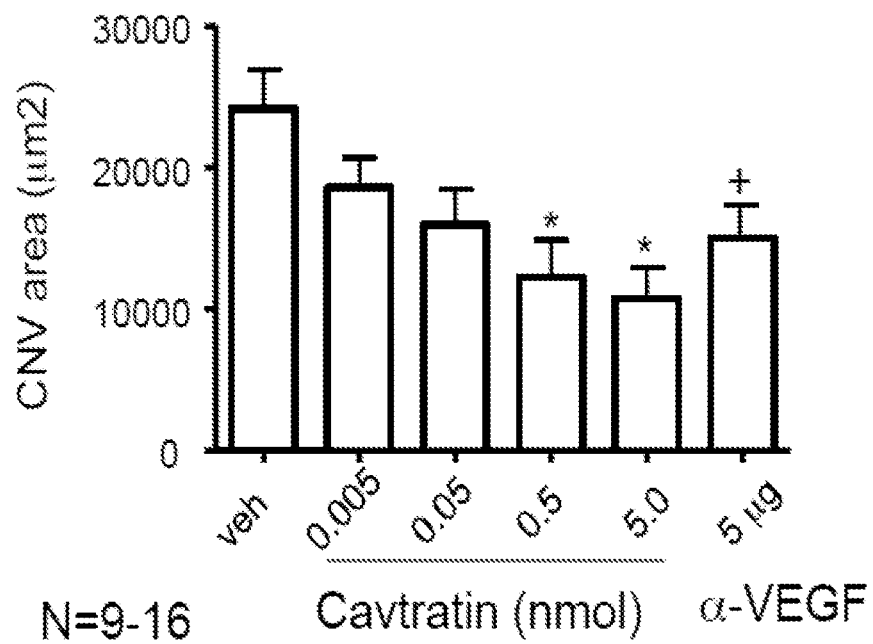

FIG. 6 illustrates the efficacy of cavtratin via intravitreal injection. In this embodiment, the rats were subjected to laser-induced neovascularization.

DETAILED DESCRIPTION OF THE INVENTION

Definitions

Abbreviations used herein have their conventional meaning within the chemical and biological arts.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the appended claims define the scope of the invention and that methods and structures within the scope of these claims and their equivalents be covered thereby.

Unless defined otherwise, all technical and scientific terms used herein have the same meaning as is commonly understood by one of skill in the art to which this invention belongs.

All patents and publications referred to herein are incorporated by reference.

The singular form "a", "an" and "the" include plural references unless the context clearly dictates otherwise.

The term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment" or "treating," or "palliating" or "ameliorating" is used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. The treatment or amelioration of symptoms can be based on objective or subjective parameters; including the results of a physical examination, functional (self) evaluation, and/or any form of vision evaluation.

The "therapeutic effect" as used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The terms "co-administration," "administered in combination with," and their grammatical equivalents, as used herein, encompass the administration of two or more agents to a subject so that both agents and/or their metabolites are present in the subject at the same time. Co-administration includes simultaneous administration in separate compositions, administration at different times in separate compositions, or administration in a composition in which both agents are present.

The term "in vivo" refers to an event that takes place in a subject's body.

The term "in vitro" refers to an event that takes places outside of a subject's body. For example, an in vitro assay encompasses any assay run outside of a subject assay. In vitro assays encompass cell-based assays in which cells alive or dead are employed. In vitro assays also encompass a cell-free assay in which no intact cells are employed.

As used herein, the term "about" when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "transport peptide" or "CPP" refers to a cell-permeable peptide, which is defined as a peptide capable of permeating and/or crossing a cell membrane.

As used herein, the term "transport construct" refers to a construct that crosses the cell membrane, wherein the construct comprises the transport peptide and at least one cargo moiety, wherein the cargo moiety crosses the cell membrane at a lower rate or to a lower degree than the transport construct. In one embodiment, the cargo moiety is selected from the group consisting of a nucleic acid; peptide; protein; oligosaccharide; lipid; glycolipid; lipoprotein; small molecule compound; therapeutic drug; UV-vis, fluorescent or radioactive label; imaging agent; diagnostic agent; prophylactic agent; liposome and virus. In another embodiment, the cargo moiety is linked to the transport peptide through a covalent or non-covalent linkage.

As used herein, the term "Endo5" refers to the peptide of SEQ ID NO. 1 or a salt thereof.

As used herein, the term "AP" refers to the peptide of SEQ ID NO. 2 or a salt thereof.

As used herein, the term "EC" refers to endothelial cell(s).

As used herein, the term "RHMVEC" refers to rat heart microvascular endothelial cell(s).

As used herein, the term "BAEC" refers to bovine aorta endothelial cell(s).

As used herein, the term "Evans blue" refers to a salt of (6E,6'E)-6,6-[(3,3'-dimethylbiphenyl-4,4'-diyl)di(1E)hydrazin-2-yl-1-ylidene]bis(4-amino-5-oxo-5,6-dihydronaphthalene-1,3-disulfonate).

As used herein, the term "binding" refers to the adherence of molecules to one another, such as, but not limited to, enzymes to substrates, antibodies to antigens, DNA strands to their complementary strands. Binding occurs because the shape and chemical nature of parts of the molecule surfaces are complementary. A common model is the "lock-and-key" used to describe how enzymes fit around their substrate. In a non-limiting example, the binding of the caveolin protein may occur at one or more domains of eNOS, such as, but not limited to, the oxygenase domain of eNOS and/or the reductase domain of eNOS.

A "disease" is a state of health of an animal wherein the animal cannot maintain homeostasis, and wherein if the disease is not ameliorated then the animal's health continues to deteriorate.

A "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

As used herein, the term "polypeptide" refers to a polymer composed of amino acid residues, related naturally occurring structural variants, and synthetic non-naturally occurring analogs thereof linked via peptide bonds. Synthetic polypeptides may be synthesized, for example, using an automated polypeptide synthesizer.

As used herein, the term "protein" typically refers to large polypeptides.

As used herein, the term "peptide" typically refers to short polypeptides. Conventional notation is used herein to represent polypeptide sequences: the left-hand end of a polypeptide sequence is the amino-terminus, and the right-hand end of a polypeptide sequence is the carboxyl-terminus.

As used herein, the term "PNA" refers to a peptide nucleic acid.

The term "amino acid sequence variant" refers to polypeptides having amino acid sequences that differ to some extent from a native sequence polypeptide. Ordinarily, amino acid sequence variants will possess at least about 70% homology, at least about 80% homology, at least about 90% homology, or at least about 95% homology to the native polypeptide. The amino acid sequence variants possess substitutions, deletions, and/or insertions at certain positions within the amino acid sequence of the native amino acid sequence.

As used herein, the terms "conservative variation" or "conservative substitution" as used herein refers to the replacement of an amino acid residue by another, biologically similar residue. Conservative variations or substitutions are not likely to change the shape of the peptide chain. Examples of conservative variations, or substitutions, include the replacement of one hydrophobic residue such as isoleucine, valine, leucine or methionine for another, or the substitution of one polar residue for another, such as the substitution of arginine for lysine, glutamic for aspartic acid, or glutamine for asparagine.

As used herein, the term "domain" refers to a part of a molecule or structure that shares common physicochemical features, such as, but not limited to, hydrophobic, polar, globular and helical domains or properties. Specific examples of binding domains include, but are not limited to, DNA binding domains and ATP binding domains.

As used herein, the term "heterologous peptide" refers to any peptide, polypeptide or protein whose sequence is selected in such a way that the product of the fusion of this sequence with the membrane translocation domain has a sequence different from the wild-type sequence flanking any membrane translocation domain.

As used herein, the term "membrane translocation domain" refers to a peptide capable of permeating the membrane of a cell and which is used to transport attached peptides into a cell in vivo.

As used herein, the term "caveolin scaffolding domain" refers to domains inclusive of putative scaffolding domains of any caveolin protein. Thus, the term as used herein is not limited to putative scaffolding domains. The complete mRNA sequence of human Cav-1 may be found at GenBank Accession No. BAG70230.1 (SEQ ID NO. 3). The complete protein code for human Cav-3 may be found at GenBank Accession No. AAC39758.1 (SEQ ID NO. 4). Additional information regarding these and other sequences described herein is publicly available from the National Center for Biotechnology Information (NCBI) at ncbi.nlm.nih.gov on the World Wide Web, which information is incorporated herein by reference.

Examples of caveolin scaffolding domains include, but are not limited to, the following: amino acids 82-101 of human caveolin-1 ($^{82}$DGIVVKASFTTFTVTKYWFYR$^{101}$) (SEQ ID NO. 5) or equivalents thereof; amino acids 82-95 of human caveolin-1 ($^{82}$DGIWKASFTTFTVT$^{95}$) (SEQ ID NO. 6) or equivalents thereof.

As used herein, the term "treatment" or "treating" is defined as the application or administration of a therapeutic agent, i.e., a compound useful within the invention (alone or in combination with another pharmaceutical agent), to a patient, or application or administration of a therapeutic agent to an isolated tissue or cell line from a patient (e.g., for diagnosis or ex vivo applications), who has a disease or disorder, a symptom of a disease or disorder or the potential to develop a disease or disorder, with the purpose to cure, heal, alleviate, relieve, alter, remedy, ameliorate, improve or affect the disease or disorder, the symptoms of the disease or disorder, or the potential to develop the disease or disorder. Such treatments may be specifically tailored or modified, based on knowledge obtained from the field of pharmacogenomics.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual" or "subject" refers to a human or a non-human mammal. Non-human mammals include, for example, livestock and pets, such as ovine, bovine, porcine, canine, feline and marine mammals. Preferably, the patient, individual or subject is human.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "composition" or "pharmaceutical composition" refers to a mixture of at least one compound useful within the invention with a pharmaceutically acceptable carrier. The pharmaceutical composition facilitates administration of the compound to a patient. Multiple techniques of administering a compound exist in the art including, but not limited to, intravenous, oral, aerosol, inhalational, rectal, vaginal, transdermal, intranasal, buccal, sublingual, parenteral, intrathecal, intragastrical, ophthalmic (including, but no limited to, intravitreal, intracameral, retrobulbar, subconjunctival, suprachoroidal, etc.), pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Exemplary Compositions

As described herein, Endo5, a short five-amino acid peptide (RRPPR—SEQ ID NO. 1), is a very potent cell-permeable peptide (CPP). Endo5 was isolated though a competitive selection process for its capacity to be quickly internalized by vascular endothelial cells and shown to increase cargo uptake by cells and increase therapeutic activity of a cargo to which it is conjugated.

As described herein, Endo5 was the most highly enriched randomly generated peptide when expressed at the surface of phages selected for the ability to be quickly internalized by endothelial cells. The maximum potency of Endo5-Cav at inhibiting VEGF-induced NO release was greater than that of AP-Cav on a similar molar basis. Further, despite its smaller size (Endo5 is a 5-mer peptide vs AP is a 16-mer acid peptide), the rate of uptake of Endo5 was three times greater than that of AP. Endo5-Cav was found to be more potent than AP-Cav at inhibiting vascular permeability in vivo.

Mechanistically, the cellular pathways involved in Endo5 uptake appear similar to that of AP. This is supported by significant co-localization between Endo5 and AP during initial endocytosis and intracellular distribution; the competitive inhibition of Endo5-Cav effect by AP; and the competitive inhibition of AP-Cav activity by Endo5. The findings reported herein provide evidence for Endo5 higher "internalization efficiency per amino acid" abilities compared to the well-established AP.

The rationale for designing a potent cell-permeable peptide for an endothelial cell resides not only in the various diseases characterized by aberrant endothelial cell activity, but also from the strategic localization of endothelial cells between the blood and underlying tissues. Following absorption, drug distribution through the vascular compartment may be quickly impaired though elimination and degradation. These normal drug inactivation mechanisms may be offset by rapid internalization at the site of action. Evidence of the magnitude of Endo5 internalization in endothelial cells, compared to the pool of randomly generated cell-permeable peptide the present system allows to test, is illustrated by its capacity to promote phage uptake in the T7 select system. This system favors rapid uptake exclusively through high affinity binding to endothelial cells, since it allows the surface expression of less than one peptide copy per phage.

Without wishing to be limited by any theory, the intracellular distribution of cargos towards their target may be at least partially, independent of the cell-permeable peptide sequence based on the fact that Cav fused to two completely different cell-permeable peptides (Endo5 or AP) attenuated eNOS activity, inhibited vascular permeability and co-localized after a two-hour "chase."

Further, it is possible that Endo5, as well as other cell-permeable peptides, may allow various exit pathways from internalization organelles and/or direct the intracellular localization of cargo molecules differently. However, the difference in uptake rate between Endo5 and AP is the likely mechanism to rationalize the difference in potency between Endo5-Cav and AP-Cay. This is supported by the data documenting the similar localization of Endo5 and AP in live cells.

On the other hand, the increase in Cav potency when fused to Endo5 and the near saturation of AP-Cav effect on eNOS activity at high doses suggest that AP-Cav effect might be limited by an overlapping rate of internalization and elimination/degradation rather than by a limitation of the pharmacophore (Cav). Without wishing to be limited by any theory, this highlights the interest in identifying highly potent CPP sequences, such as sequences comprising Endo5.

In various embodiments, the invention described herein includes an isolated transport peptide that crosses a cell membrane. In one embodiment, the peptide comprises the amino acid sequence RRPPR (SEQ ID NO. 1). In another embodiment, the transport peptide consists essentially of SEQ ID NO. 1. In yet another embodiment, the transport peptide consists of SEQ ID NO. 1. In yet another embodiment, the transport peptide selectively binds to a target cell or crosses a cell membrane. In yet another embodiment, the cell comprises an endothelial cell, a cardiac cell, a skeletal muscle cell or a brain cell.

In one aspect, the invention provides a pharmaceutical composition comprising a transport peptide comprising SEQ ID NO. 1 and a pharmaceutically acceptable carrier. In yet another embodiment, the cell comprises an endothelial cell, a cardiac cell, a skeletal muscle cell or a brain cell. In yet another embodiment, the cell consists of an endothelial cell, a cardiac cell, a skeletal muscle cell or a brain cell.

The invention further includes a transport construct comprising the peptide of the invention and a cargo moiety.

In one embodiment, the transport construct comprises a cargo moiety linked to a transport peptide comprising SEQ ID NO. 1. In another embodiment, the transport peptide consists of SEQ ID NO. 1. In yet another embodiment, the cargo moiety is at least one selected from the group consisting of a nucleic acid (and analogues thereof, such as a peptide nucleic acid or "PNA"); peptide; protein; oligosaccharide; lipid; glycolipid; lipoprotein; therapeutic drug; UV-vis, fluorescent or radioactive label; imaging agent; diagnostic agent; prophylactic agent; liposome and virus (such as T-7 bacteriophage).

In one embodiment, the cargo moiety is at least one selected from the group consisting of SEQ ID NOs. 3-6 and 11-19. In another embodiment, the transport construct comprises at least one sequence selected from the group consisting of:

SEQ ID NO. 1-SEQ ID NO. 3
SEQ ID NO. 1-SEQ ID NO. 4
SEQ ID NO. 1-SEQ ID NO. 5
SEQ ID NO. 1-SEQ ID NO. 6
SEQ ID NO. 1-SEQ ID NO. 11
SEQ ID NO. 1-SEQ ID NO. 12
SEQ ID NO. 1-SEQ ID NO. 13
SEQ ID NO. 1-SEQ ID NO. 14
SEQ ID NO. 1-SEQ ID NO. 15
SEQ ID NO. 1-SEQ ID NO. 16
SEQ ID NO. 1-SEQ ID NO. 17
SEQ ID NO. 1-SEQ ID NO. 18
SEQ ID NO. 1-SEQ ID NO. 19
SEQ ID NO. 3-SEQ ID NO. 1
SEQ ID NO. 4-SEQ ID NO. 1
SEQ ID NO. 5-SEQ ID NO. 1
SEQ ID NO. 6-SEQ ID NO. 1
SEQ ID NO. 11-SEQ ID NO. 1
SEQ ID NO. 12-SEQ ID NO. 1
SEQ ID NO. 13-SEQ ID NO. 1
SEQ ID NO. 14-SEQ ID NO. 1
SEQ ID NO. 15-SEQ ID NO. 1
SEQ ID NO. 16-SEQ ID NO. 1
SEQ ID NO. 17-SEQ ID NO. 1
SEQ ID NO. 18-SEQ ID NO. 1
SEQ ID NO. 19-SEQ ID NO. 1

In yet another embodiment, the transport construct is selected from the group consisting of:

SEQ ID NO. 1-SEQ ID NO. 3
SEQ ID NO. 1-SEQ ID NO. 4

-continued

SEQ ID NO. 1-SEQ ID NO. 5
SEQ ID NO. 1-SEQ ID NO. 6
SEQ ID NO. 1-SEQ ID NO. 11
SEQ ID NO. 1-SEQ ID NO. 12
SEQ ID NO. 1-SEQ ID NO. 13
SEQ ID NO. 1-SEQ ID NO. 14
SEQ ID NO. 1-SEQ ID NO. 15
SEQ ID NO. 1-SEQ ID NO. 16
SEQ ID NO. 1-SEQ ID NO. 17
SEQ ID NO. 1-SEQ ID NO. 18
SEQ ID NO. 1-SEQ ID NO. 19
SEQ ID NO. 3-SEQ ID NO. 1
SEQ ID NO. 4-SEQ ID NO. 1
SEQ ID NO. 5-SEQ ID NO. 1
SEQ ID NO. 6-SEQ ID NO. 1
SEQ ID NO. 11-SEQ ID NO. 1
SEQ ID NO. 12-SEQ ID NO. 1
SEQ ID NO. 13-SEQ ID NO. 1
SEQ ID NO. 14-SEQ ID NO. 1
SEQ ID NO. 15-SEQ ID NO. 1
SEQ ID NO. 16-SEQ ID NO. 1
SEQ ID NO. 17-SEQ ID NO. 1
SEQ ID NO. 18-SEQ ID NO. 1
SEQ ID NO. 19-SEQ ID NO. 1

In another embodiment, the compositions further comprise a pharmaceutically acceptable carrier.

The cargo moiety may be combined with or linked to the transport peptide to form the transport construct of the present invention. The transport peptide and the cargo moiety are combined or linked in such a manner that they remain combined or linked under the conditions in which the transport construct is used (e.g., under conditions in which the transport construct is administered to an individual). In one embodiment, the cargo moiety is covalently linked to the transport peptide through a linker or a chemical bond. Alternatively, the transport peptide and the cargo moiety are combined through a noncovalent linkage, such as electrostatic and/or hydrophobic interaction.

The invention includes functionally equivalent variants of peptides described elsewhere herein. Such variants include peptides with amino acid substitutions that maintain the functional integrity of the original peptide. Examples of amino acid substitutions include those that result in changes to the peptide wherein similar charge, polarity, hydrophobicity or structure of the original amino acid is maintained. Peptide variants also include peptide mimetics. Peptide mimetics include chemically modified peptides and peptide-like molecules containing non-naturally occurring amino acids.

In one embodiment, the peptides of the present invention may be obtained from sources in which they occur in nature or produced using known techniques, such as chemical synthesis or genetic engineering methods (e.g., recombinant DNA or RNA technology). In another embodiment, the peptides of the invention may be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

In one embodiment, isolated peptides of the present invention are relatively free from unrelated peptides, as well as contaminating polypeptides, lipids, nucleic acids and other cellular material that normally are associated with the peptide in a cell or that are associated with the peptide in a library.

The transport constructs of the invention are useful for the delivery of cargo moieties across the cell membrane. The transport constructs of the invention are also useful for the delivery of cargo moieties to a target cell (e.g., a specific cell type, such as a cardiac cell) and for the delivery of cargo moieties to a target cell and/or across the membrane of the target cell.

The transport peptides of the present invention have the ability to cross the cell membrane of a cell (e.g., internalize into the cell). For example, in one embodiment of the invention, a transport peptide translocates from the extracellular environment of a cell, penetrates the lipid bilayer of the cell membrane, and crosses the cell membrane into the intracellular environment of the cell. In another embodiment, the transport peptides of the present invention selectively bind to a target cell. In yet another embodiment, the transport peptides selectively bind to and cross the cell membrane of a target cell. A target cell is a specific cell type such as, for example, a cardiac cell, a skin cell (e.g., an endothelial cell), a skeletal muscle cell or a brain cell (e.g. a neuron) but may be any cell, including human and non-human cells.

In a non-limiting example, a transport peptide of the invention is linked to a cargo moiety and transports the cargo moiety across the cell membrane of a cell. For example, in one embodiment, a protein, such as caveolin or a transcription factor, linked to a transport peptide is carried from the extracellular environment of a cell and transported across the cell membrane and into the intracellular environment of the cell. In another embodiment, a transport peptide of the invention linked to a cargo moiety selectively binds the cargo moiety to a target cell (e.g., a cardiac cell). In yet another embodiment, the transport peptide linked to a cargo moiety selectively binds the cargo moiety to a target cell (e.g., a cardiac cell), and transports the cargo moiety from the extracellular environment of the target cell across the cell membrane and into the intracellular environment of the target cell.

In one embodiment, the cargo moiety comprises an organic or inorganic compound. The organic compound may be isolated from nature (e.g., from cells in which it occurs) or may be produced using known methods, such as genetic engineering methods (e.g., recombinant DNA or RNA technology) or chemical synthetic methods. For example, an organic molecule may be an RNA molecule, polypeptide or a fragment thereof, which may be isolated from a cell, expressed from a recombinant nucleic acid molecule or synthesized chemically. An organic molecule also can be a non-naturally occurring molecule. A non-limiting example of a non-naturally occurring molecule is a nucleic acid sequence containing non-naturally occurring nucleoside analogs or phosphorothioate bonds that link the nucleotides and protect against degradation by nucleases. A ribonucleotide containing a 2-methyl group, instead of the normal hydroxyl group, bonded to the 2'-carbon atom of ribose residues, is an example of a non-naturally occurring RNA molecule that is resistant to enzymatic and chemical degradation. Other examples of non-naturally occurring organic molecules include RNA containing 2'-aminopyrimidines (wherein such RNA is 1,000 times more stable in human serum and urine as compared to naturally occurring RNA; Lin et al., 1994, Nucl. Acids Res. 22:5229-5234, and Jellinek et al., 1995, Biochemistry, 34:11363-11372).

In one embodiment, the cargo moiety comprises a DNA, a RNA or a nucleic acid analog. The DNA or RNA may be an oligo(deoxy)nucleotide of any length. Such nucleic acid molecules may be linear, circular or supercoiled; may be single-stranded or double-stranded DNA or RNA; or may be a DNA/RNA hybrid. Nucleic acid analogs include charged and uncharged backbone analogs, such as phosphonates (e.g., methyl phosphonates), phosphoramidates (N3' or N5'), thiophosphates, uncharged morpholino-based polymers, and peptide nucleic acids (PNAs). Such molecules may be used in a variety of therapeutic regimens, including enzyme replacement therapy, gene therapy and anti-sense therapy, for example. Peptide nucleic acids (PNAs) are analogs of DNA. The backbone of a PNA is formed by peptide bonds rather than phosphate esters, making it well-suited for anti-sense applications. Since the backbone is uncharged, PNA/DNA or PNA/RNA duplexes exhibit greater than normal thermal stability. PNAs have the additional advantage that they are not recognized by nucleases or proteases. PNAs may be synthesized on an automated peptides synthesizer using standard t-Boc chemistry. The PNA may be linked to a transport peptide of the invention using known methods in the art.

In one embodiment, the cargo moiety is a polypeptide. In another embodiment, the cargo moiety comprises caveolin or a fragment thereof. In yet another embodiment, the cargo moiety is a transcription factor or a nuclear localization peptide. In yet another embodiment, two cargo moieties, one comprising a transcription factor and the other comprising a nuclear localization peptide, are present in the transport construct of the invention.

In one embodiment, the cargo moiety comprises a label, such as a dye or a radioactively labeled compound. In another embodiment, the cargo moiety comprises rhodamine. In yet another embodiment, the cargo moiety comprises a marker, such as green fluorescent protein, blue fluorescent protein, yellow fluorescent protein, biotin or mixtures thereof.

In a non-limiting example, recombinant techniques may be used to covalently attach a transport peptide to a cargo moiety, such as joining DNA or RNA coding for the transport peptide with DNA or RNA coding for the cargo moiety and expressing the encoded products in an appropriate host cell (a cell capable of expressing the transport construct). Alternatively, the two separate nucleotide sequences may be expressed in a cell or can be synthesized chemically and subsequently combined, using known techniques. Alternatively, the transport peptide-cargo moiety may be synthesized chemically as a single amino acid sequence and, thus, combining them is not needed.

In one embodiment, when there is more than one cargo moiety linked to the transport peptide, the more than one moiety may be the same or different. In another embodiment, the cargo moiety or moieties are linked to the transport peptide at either the N- or C-terminus of the transport peptide. In the case wherein there are at least two cargo moieties linked to the transport peptide, one cargo moiety may be linked at the N-terminus of the transport peptide and one cargo moiety may be linked at the C-terminus of the transport peptide. Alternatively, more than one cargo moiety may be linked to either the N- or C-terminus of the transport peptide.

In one embodiment, the cargo moiety may be linked to a transport peptide of the present invention either directly (i.e., through a chemical bond) or indirectly by means of a linker. Linkers include, for example, one or more amino acid residues. The linker may be, for example, a short sequence of 10 amino acid residues (e.g., 1 to 10, 1 to 5 or 1 to 4 amino acid residues), and may optionally include a cysteine residue through which the linker binds to the transport peptide or cargo moiety of the transport construct. A linker may also be a group such as a sulfydryl group or carboxyl group.

Suitable linkers include bi- and multi-functional alkyl, aryl, aralkyl or peptidic moieties, alkyl, aryl or aralkyl aldehydes, acids, esters and anhydrides, sulfydryl or carboxyl groups, such as maleimido benzoic acid derivatives, maleimido proprionic acid derivatives and succinimido derivatives, or may be derived from cyanuric bromide or chloride, carbonyldiimidazole, succinimidyl esters or sulfonic halides. The functional groups on the linker used to form covalent bonds between linker and cargo moiety on the one hand, as well as linker and transport peptide on the other hand, may be two or more of e.g., amino, hydrazine, hydroxyl, thiol, maleimido, carbonyl, and carboxyl groups.

In one embodiment, the transport construct may dissociate in vitro or in vitro into the cargo moiety and transport peptide by way of chemical or enzymatic cleavage. In another embodiment, the linker comprises amino acid residues, and the in vitro or in vivo cleavage occurs within the linker.

In one embodiment, wherein the cargo moiety is a polypeptide, the cargo moiety is linked to the transport peptide as a fusion protein by means of recombinant technology. A fusion protein is the co-linear, covalent linkage of two or more proteins via their polypeptide backbones, through genetic expression of a nucleic acid molecule encoding those proteins. The nucleic acid encoding the cargo moiety of the fusion protein is in-frame with the nucleic acid encoding the transport peptide. "In-frame" indicates that the nucleic acid sequence encoding the cargo moiety is in the correct reading frame as the nucleic acid sequence encoding the transport peptide. Therefore, the correct amino acid sequences are translated for both the transport peptide and cargo moiety of the fusion protein.

In one embodiment, the cargo moiety is conjugated to the transport peptide via chemical cross-linking. Numerous chemical cross-linking methods are known and useful for linking the transport peptides of this invention to a cargo moiety. Coupling of the cargo moiety and the transport peptide may be accomplished via a coupling or linking agent. Intermolecular cross-linking reagents that may be utilized are exemplified in Means & Feeney, Chemical Modification of Proteins, Holden-Day, 1974, pp. 39-43, and Wong, Chemistry of Protein Conjugation and Cross-Linking, CRC Press (1991). Among these reagents are, for example, N-succinimidyl 3-(2-pyridyldithio) propionate ("SPDP") or N,N'-(1,3-phenylene) bismaleimide (both of which are highly specific for sulfydryl groups and form irreversible linkages); N,N'-ethylene-bis-(iodoacetamide) or other such reagent having 6 to 11 carbon methylene bridges (which are relatively specific for sulfhydryl groups); and 1,5-difluoro-2,4-dinitrobenzene (which forms irreversible linkages with amino and tyrosine groups).

Other cross-linking reagents useful for this purpose include: p,p'-difluoro-m,m'-dinitrodiphenylsulfone (which forms irreversible cross-linkages with amino and phenolic groups); dimethyl adipimidate (which is specific for amino groups); phenol-1,4-disulfonylchloride (which reacts principally with amino groups); hexamethylenediisocyanate or diisothiocyanate, or azophenyl-p-diisocyanate (which reacts mainly with amino groups); glutaraldehyde (which reacts with different side chains) and disdiazobenzidine (which reacts primarily with tyrosine and histidine).

In one embodiment, the cross-linking reagents yield a transport construct that is essentially non-cleavable under cellular conditions. In another embodiment, the cross-linking reagent contains a covalent bond, such as a disulfide, that is cleavable under cellular conditions. For example, dithiobis(succinimidylpropionate) ("DSP"), Traut's reagent and N-succinimidyl 3-(2-pyridyldithio) propionate ("SPDP") are well-known cleavable cross-linkers. The use of a cleavable cross-linking reagent permits the transport peptide to separate from the cargo moiety after delivery into the target cell. A construct comprising a direct disulfide linkage may also be useful within the methods of the invention. In one embodiment, the cross-linking reagent such as N-gamma-maleimidobutyryloxy-succinimide ester ("GMBS") and sulfo-GMBS have reduced immunogenicity.

The present invention further includes a composition comprising an isolated nucleic acid molecule that encodes the polypeptide having the fusion peptides and conservative nucleotide substitutions thereof, preferably in isolated form to generate the compositions of the invention. Conservative nucleotide substitutions include nucleotide substitutions that do not affect the coding for a particular amino acid as most amino acids have more than one codon. Conservative nucleotide substitutions thus also include silent mutations and differential codon usage.

In one embodiment, the nucleic acid encodes a transport peptide comprising SEQ ID NO. 1. In another embodiment, the nucleic acid encodes a transport peptide consisting of SEQ ID NO. 1. In another embodiment, the nucleic acid comprises 5'-CGGCGCCCGCCTCGT-3' (SEQ ID NO. 7)

In one embodiment, the composition further comprises a nucleic acid encoding at least one cargo moiety. In another embodiment, the cargo moiety is selected from the group consisting of a peptide; a protein; a biologically active compound; a label; an imaging agent; a diagnostic agent; a therapeutic agent; and a prophylactic agent. In yet another embodiment, the cargo moiety comprises at least one selected from the group consisting of SEQ ID NOs: 3-6. In yet another embodiment, the composition further comprises a pharmaceutically acceptable carrier.

The invention further includes an expression vector and an isolated host cell comprising nucleic acid encoding a peptide comprising SEQ ID NO. 1. In one embodiment, the peptide consists of SEQ ID NO. 1.

The invention also includes an expression vector and an isolated host cell comprising nucleic acid encoding a cargo moiety linked to the peptide comprising SEQ ID NO. 1. In one embodiment, the peptide consists of SEQ ID NO. 1.

In one embodiment, the transport construct comprises a fusion protein. In another embodiment, the vector or host cell further comprises transcriptional activation elements that allow for the expression of the nucleic acid encoding the transport peptide. Expression system vectors, which incorporate the necessary regulatory elements for protein expression, as well as restriction endonuclease sites that facilitate cloning of the desired sequences into the vector, are known to those skilled in the art. In one embodiment, the cargo moiety is in-frame with the nucleic acid encoding the transport peptide.

In a non-limiting example, a recombinant DNA expression vector containing the elements previously described is introduced into an appropriate host cell (i.e., a cell capable of expressing the transport construct) where cellular mechanisms of the host cell direct the expression of the fusion protein encoded by the recombinant DNA expression vector. Alternately, cell-free systems known to those skilled in the art may be used for expression of the fusion protein.

The purified fusion protein produced by the expression vector host cell system may then be administered to the target cell, where the transport peptide mediates the import of the fusion protein through the cell membrane of the target cell into the interior of the cell. A target cell is a specific cell type such as, for example, a cardiac cell, a skin cell, such as an epithelial cell; a skeletal muscle cell or a brain cell (e.g., a neuron), but may be any cell, including human and nonhuman cells.

An expression vector host cell system may be selected from among a number of such systems known to those skilled in the art. In one embodiment, the fusion protein may be expressed in isolated host cells, such as *Escherichia coli*. In another embodiment, fusion proteins may be expressed in other bacterial expression systems, viral expression systems, eukaryotic expression systems, or cell-free expression systems. Cellular hosts used by those skilled in the art include, but are not limited to, isolated host cells such as, for example, *Bacillus subtilis*, yeast such as *Saccharomyces cerevisiae, Saccharomyces carlsbergenesis, Saccharomyces pombe*, and *Pichia pastoris*, as well as mammalian cells such as NIH3T3, HeLa, HEK293, HUVEC, rat aortic smooth muscle cells and adult human smooth muscle cells. The expression vector selected by one skilled in the art includes transcriptional activation elements such as promoter elements and other regulatory elements appropriate for the host cell or cell-free system in which the fusion protein will be expressed. In mammalian expression systems, for example, suitable expression vectors may include DNA plasmids, DNA viruses, and RNA viruses. In bacterial expression systems, suitable vectors may include plasmid DNA and bacteriophage vectors.

Non-limiting examples of specific expression vector systems include the pBAD/gIII vector (Invitrogen, Carlsbad, Calif.) system for protein expression in *E. coli*, which is regulated by the transcriptional regulator AraC. An example of a vector for mammalian expression is the pcDNA3.1/V5-His-TOPO eukaryotic expression vector (Invitrogen). In this vector, the transport construct maybe expressed at high levels under the control of a strong cytomegalovirus (CMV) promoter. A C-terminal polyhistidine ($His_6$) tag enables transport construct purification using nickel-chelating resin. Secreted protein produced by this vector may be detected using an anti-His (C-term) antibody.

A baculovirus expression system may also be used for production of a transport construct comprising the transport peptide and a cargo moiety wherein the cargo moiety is a polypeptide. A commonly used baculovirus is AcMNPV. Cloning of the transport construct DNA may be accomplished by using homologous recombination. In a non-limiting example, the transport construct DNA sequence is cloned into a transfer vector containing a baculovirus promoter flanked by baculovirus DNA, particularly DNA from the polyhedrin gene. This DNA is transfected into insect cells, where homologous recombination occurs to insert the transport construct DNA into the genome of the parent virus. Recombinants are identified by altered plaque morphology.

Many transport constructs in which the cargo moiety is a peptide or protein that may not be appropriately post-translationally modified in bacterial expression systems may instead be expressed with baculovirus vectors. Enzymes, signaling molecules, mediators of cell cycle control, transcription factors, antigenic peptides, full-length protein products of viral, bacterial, or other origin for use in vaccine therapy, protein products of human cells for use in cancer vaccine therapy, toxins, and proteins involved in intracellular signaling systems that may not be appropriately post-translationally modified in bacterial expression systems may be expressed with baculovirus vectors.

Proteins as described above may also be produced by the method of the present invention by mammalian viral expression systems. An ecdysone-inducible mammalian expression system (Invitrogen, Carlsbad, Calif.) may also be used to express the transport construct wherein the transport construct is a fusion protein.

In one embodiment, yeast host cells, such as *Pichia pastoris*, may be used for the production of a transport construct by the method of the present invention. Expression of heterologous proteins from plasmids transformed into *Pichia* has been described by U.S. Pat. No. 5,002,876 to Sreekrishna et al. Vectors for expression in *Pichia* of a fusion protein comprising a transport peptide of the present invention and a cargo moiety wherein the cargo moiety is a peptide or protein are commercially available as part of a *Pichia* Expression Kit (Invitrogen, Carlsbad, Calif.).

Purification of heterologous protein produced in *Pichia* was described by U.S. Pat. No. 5,004,688 to Craig et al., and techniques for protein purification from yeast expression systems are well known to those skilled in the art. In the *Pichia* system, commercially available vectors may be selected from among those that are more suited for the production of cytosolic, non-glycosylated proteins and those that are more suited for the production of secreted, glycosylated proteins, or those directed to an intracellular organelle, so that appropriate protein expression may be optimized for the cargo moiety of choice that is a polypeptide.

Exemplary Methods of Use

The invention described herein includes a method of delivering a cargo moiety to or into a target cell. In one embodiment, the method comprises contacting the target cell with a transport construct, wherein the transport construct comprises a cargo moiety and a transport peptide comprising the amino acid sequence SEQ ID NO. 1, whereby the cargo moiety is delivered to or into the target cell.

In some embodiments, the cargo moiety is covalently linked to the transport peptide through a linker or a chemical bond. In other embodiments, the transport peptide consists of SEQ ID NO. 1. In yet other embodiments, the cargo moiety is at least one selected from the group consisting of a nucleic acid; a peptide; a protein; an oligosaccharide; a lipid; a glycolipid; a lipoprotein; a small molecule compound; a therapeutic drug; an UV-vis, fluorescent or radioactive label; an imaging agent; a diagnostic agent; a prophylactic agent; a liposome and a virus. In still other embodiments, the target cell comprises an endothelial cell, a cardiac cell, a skeletal muscle cell or a brain cell. In yet another embodiment, the cell is mammalian. In yet another embodiment, the mammal is human.

The invention further includes a method of delivering a cargo moiety to or into a target cell of a subject in need thereof. In one embodiment, the method comprises administering to the subject a therapeutically effective amount of a pharmaceutically acceptable composition comprising a transport construct, wherein the transport construct comprises the cargo moiety and a transport peptide comprising the amino acid sequence SEQ ID NO. 1, whereby the cargo moiety is delivered to or into the target cell of the subject.

In one embodiment, the cargo moiety is covalently linked to the transport peptide through a linker or a chemical bond. In another embodiment, the transport peptide consists of SEQ ID NO. 1. In yet another embodiment, the cargo moiety is at least one selected from the group consisting of a nucleic acid; a peptide; a protein; an oligosaccharide; a lipid; a glycolipid; a lipoprotein; a small molecule compound; a therapeutic drug; an UV-vis, fluorescent or radioactive label; an imaging agent; a diagnostic agent; a prophylactic agent; a liposome and a virus. In yet another embodiment, the target cell comprises an endothelial cell, a cardiac cell, a skeletal muscle cell or a brain cell. In yet another embodiment, the composition is administered by at least one route selected from the group consisting of intravenous, oral, inhalational, rectal, vaginal, transdermal, intranasal, buccal, sublingual, parenteral, intrathecal, intragastrical, ophthalmic, pulmonary and topical. In yet another embodiment, the subject is a mammal. In yet another embodiment, the mammal is human.

The method according to the invention described includes the treatment/prevention of one or more diseases including, but not limited to, rheumatoid arthritis (RA), psoriasis, psoriatic arthritis, systemic lupus erythematosus (SLE), lupus nephritis, type I diabetes, Grave's disease, Inflammatory bowel disease (IBD), Crohn's disease (CD), ulcerative colitis (UC), irritable bowel syndrome, multiple sclerosis (MS), neuromyelitis optica (NMO), autoimmune myocarditis, Kawasaki disease, coronary artery disease, chronic obstructive pulmonary disease (COPD), interstitial lung disease, autoimmune thyroiditis, scleroderma, systemic sclerosis, osteoarthritis, atoptic dermatitis, vitiligo, graft vs. host disease, Sjogren's syndrome, autoimmune nephritis, Goodpasture's syndrome, chronic inflammatory demyelinating polyneuropathy, ANCA-associated vasculitis, uveitis, scleroderma, bullous pemphigoid, Alzheimer's Disease, amyotrophic lateral sclerosis, Huntington's Chorea, cystic fibrosis, gout, age-related macular degeneration, allergy, asthma and other autoimmune diseases that are a result of either acute or chronic inflammation.

In a further embodiment the disease or disorder is an acute or chronic inflammation, wherein the disorder may be an auto-immune disease. In an embodiment the disorder is rheumatoid arthritis (RA), psoriatic arthritis, systemic lupus erythematosus (SLE), lupus nephritis, inflammatory bowel disease (IBD) including Crohn's disease (CD) or ulcerative colitis (UC) or irritable bowel syndrome (IBS). In further embodiments the disorder is RA or SLE. Apart from chronic diseases, the compositions described herein may be relevant in relation to acute indications such as transplantation, ischemia/reperfusion injury (e.g. acute myocardial infarction, stroke), sepsis (e.g. SIRS, MODS, ALI), atherosclerosis and intracerebral haemorrhage (ICH).

Exemplary Autoimmune Diseases

In various embodiments the compositions described herein are useful to treat one or more autoimmune diseases.

"Autoimmune disease" refers to a disease caused by an inability of the immune system to distinguish foreign molecules from self-molecules, and a loss of immunological tolerance to self-antigens, which results in destruction of the self-molecules. Non-limiting examples of autoimmune diseases include but are not limited to systemic lupus erythematosus, Sjogren's syndrome, scleroderma, ulcerative colitis, insulin-dependent diabetes mellitus (IDDM), multiple sclerosis (MS), neuromyelitis optica (NMO), and rheumatoid arthritis.

In specific embodiments, the autoimmune disease is multiple sclerosis, thyroiditis, type 1 diabetes, sarcoidosis, psoriasis, allergic rhinitis, atopic dermatitis, myasthenia gravis, inflammatory bowel disease including Crohn's disease and ulcerative colitis (UC), systemic lupus erythematosis (SLE), arthritis, osteoarthritis, rheumatoid arthritis, osteoporosis, asthma and chronic obstructive pulmonary disease (COPD).

Other autoimmune diseases include, for example multiple sclerosis, neuromyelitis optica, systemic lupus erythematosis, inflammatory bowel diseases (IBD), Crohn's disease, irritable bowel syndrome, pancreatitis, ulcerative colitis, diverticulosis, myasthenia gravis, vasculitis, psoriasis, scleroderma, asthma, allergy, systemic sclerosis, vitiligo, arthritis such as osteoarthritis, juvenile rheumatoid arthritis, ankylosing spondylitis, Kawasaki disease, temporal arteritis, Gullian Barre syndrome, and inflammatory optic neuropathy.

Exemplary Inflammatory Diseases

In various embodiments, the compositions described herein are useful to treat or prevent one or more inflammatory diseases or disorders.

The inflammatory response is not necessarily associated with external stimuli, or may be caused by a non-harmful environmental substances (in case of allergies). In both cases an over-expression of pro-inflammatory cytokines without proper controls leads to inflammation which is the hallmark of topical and systemic inflammation generally, as well as a variety of inflammatory diseases and disorders.

Inflammation is associated with a variety of disorders such as eczema and dermatitis, including for example, atopic dermatitis, seborrheic dermatitis, dyshidrotic eczema, nummular dermatitis, stasis dermatitis, allergic dermatitis, psoriasis, pruritus, multiple sclerosis, neuromyelitis optica, cutaneous inflammation, cicatricial pemphigoid, scleroderma, hidradenitis suppurativa, toxic epidermal necrolysis, acne, osteitis, graft vs. host disease (GvHD), pyroderma gangrenosum, and Behcet's Syndrome.

Inflammatory diseases of the eye including conjunctivitis, uveitis, iritis, scleritis.

Inflammatory diseases of the respiratory tract including the upper respiratory tract such as rhinitis and sinusitis and inflammatory diseases of the lower respiratory tract including bronchitis.

Inflammatory myopathy such as myocarditis.

Other inflammatory diseases such as ischemia reperfusion injuries related to an inflammatory ischemic event such as a stroke or cardiac arrest.

Other inflammatory conditions such as systemic inflammatory response syndrome (SIRS) and sepsis.

In specific embodiments, the inflammatory disease or disorder is selected from the group consisting of psoriasis, multiple sclerosis, rheumatoid arthritis, osteoarthritis, systemic lupus erythematosus, Hashimoto's thyroidis, myasthenia gravis, diabetes type I or II, asthma, inflammatory lung injury, inflammatory liver injury, inflammatory glomerular injury, atopic dermatitis, allergic contact dermatitis, irritant contact dermatitis, seborrhoeic dermatitis, Sjoegren's syndrome, keratoconjunctivitis, uveitis, inflammatory bowel disease, Crohn's disease, ulcerative colitis, an inflammatory disease of the joints, skin, or muscle, acute or chronic idiopathic inflammatory arthritis, myositis, a demyelinating disease, chronic obstructive pulmonary disease, interstitial lung disease, interstitial nephritis and chronic active hepatitis.

Uveitis

Uveitis affects more than half a million people in the US and the chronic form drives 5-20% of blindness. Better therapies for uveitis are needed to reduce both acute inflammatory process and progressive visual loss. In particular, therapies that reduce inflammation and visual loss without the significant tolerability issues associated with current therapies would drive better vision in both the short and long terms for uveitis patients.

The goal of immunosuppressive therapy is to alleviate the acute inflammatory events in the eye. Suppression of inflammation in chronic uveitis often involves high dose systemic steroid treatment that can be prolonged. Even in quiescent eyes, intravitreal steroid improves vision. However, steroids at these doses have a significant adverse event (AE) profile.

Many of the systemic AEs may be avoided by using intravitreal sustained release steroid preparations (Ozurdex, Retisert, etc). These approaches do not avoid the ocular AEs of steroids including the vision threatening AEs of cataract and glaucoma. Steroids often achieve short term control of inflammation, but not control of the disease, with recurrences of inflammation and the need for additional immunosuppressive therapies common in this population.

Uveitis is a collection of conditions all having inflammation of the uveal tract (iris, ciliary body and choroid) in common but often involving the retina. Current treatment goals are the suppression of inflammation using steroids in combination with immunomodulators such as methotrexate, mycophenylate mofetil, and biologic modifiers including anti-TNFs. For the 60,000 chronic posterior and pan uveitis patients in the US, treatment with high dose systemic steroids is predominant with average daily doses of steroid>40 mg/day, substantially in excess of the SUN guidelines and sufficient to cause significant adverse events, some of which are vision threatening themselves.

The use of immunomodulators has added significantly to the treatment options available, and most chronic uveitis patients are treated with combinations. However, while these treatments do have beneficial effect, a significant fraction of uveitis patients lose vision despite treatment. In one study, 58% of panuveitis patients experienced visual loss and almost 10% were bilaterally blind.

Key components of the inflammatory process in uveitis include the invasion of the eye by T-cells and macrophages, breakdown of the blood-retinal barrier (BRB), edema, release of cytokines, and leakage of protein into the aqueous and vitreous. Since many inflammatory pathways are activated in uveitis and the underlying causes of uveitis span a broad array of inflammatory conditions from juvenile idiopathic arthritis to Bechets disease to sarcoid, it is unlikely that a therapeutic approach that is highly specific for a single pathway will be efficacious across most uveitis patients. A more promising approach is to modulate cellular processes common to multiple pathways.

Many of the key inflammatory cells signaling pathways are regulated through a cellular structure known as caveolae. Caveolae and the key coat protein caveolin-1 are involved in the transduction of cytokine and growth factor signals regulating vascular barrier function and angiogenesis, including but not limited to activation of NO synthase and VEGF receptors. At the molecular level, these signaling events are dependent on protein-protein interactions between caveolin and its binding partners.

Since caveolin-protein interactions are intracellular, molecules targeting this process must be cell penetrant. The caveolin mimetic cavtratin, a fusion peptide of a cell penetrating peptide to the scaffolding domain of cavtratin inhibits the activation of NO and other signals mediated via caveolae. Cavtratin reduces the permeability of vessels, antagonizes the ability of the cytokine CCL2 to promote monocytic transit of the blood-brain barrier (BBB), reduces MMP expression, suppresses the actions of both NGF (via TrkA) and VEGF and inhibits angiogenesis.

In certain embodiments, provided herein is a novel therapy for uveitis based upon modulation of caveolar function via the use of hybrid cell penetrating-caveolin domain (cavtratin) peptides that block vascular permeability. A first generation cavtratin has been shown to block edema and inflammatory cell invasion and to improve clinical score in an experimental model of autoimmune encephalitis.

This novel therapeutic approach to treat uveitis modulates caveolin's role in signal transduction and to leverage the role that the vascular endothelial cells play in regulating the immune response, a role that is particularly important in the eye and brain where a significant blood-tissue barrier is maintained and regulated by the vascular endothelial cells.

The methods provided herein are innovative at the cellular level, targeting vascular endothelial cell function to modulate inflammatory processes at the molecular level—the molecular mechanism is not an anti-inflammatory per se, but in the manipulation of caveolin function within endothelial cells that play a key role in the gatekeeper function of the blood retina barrier (BRB). By inhibiting caveolin-dependent signaling, the transmission of signals from a variety of growth factors and cytokines is inhibited, and the breakdown of the blood brain barrier (BBB) and transmigration of immune cells into the retina is suppressed.

Figure 1:
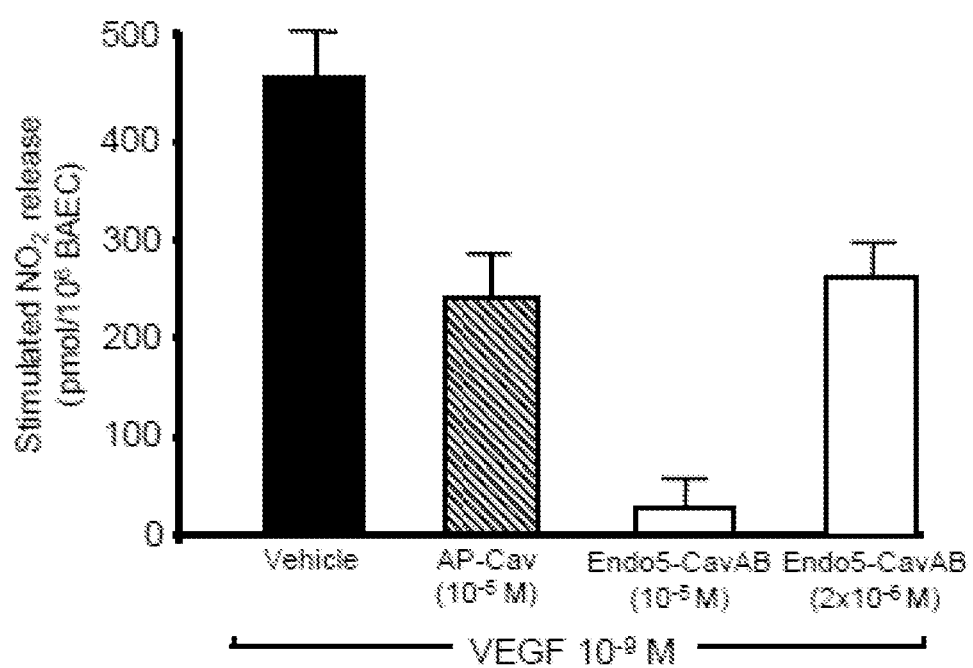
FIG. 1 illustrates the exponential enrichment of cell-permeable phage during biopanning. The percentages of recovered phage are plotted for the six rounds of biopanning in endothelial cells. Exponential correlation is established with a $R^2$ value of 0.975.

The compositions provided herein also bring novelty to the invention described. In a specific embodiment, Endo5-CavAB (SEQ ID NO. 1/SEQ ID NO. 6) is used. This molecule is a cell penetrating peptide that uses a novel short sequence discovered by phage display to promote internalization. This short peptide has been coupled to a fragment of the caveolin scaffold that is optimized for efficiency and is able to produce a more robust effect than caveolin at a lower concentration (FIG. 1). Endo5-CavAB is thus an example of an optimized, second generation cavtratin that is more potent than cavtratin.

The compositions provided herein can be administered via any suitable route. In specific embodiments, the composition is provided to a subject via systemic (i.p.) administration or intravitreal (IVT) administration.

Multiple Sclerosis (MS)

Another example of inflammatory disease is Multiple Sclerosis (MS). MS is a chronic and unpredictable inflammatory disease of the CNS, which may affect the brain and spinal cord that commonly affects young adults. Hafler et al. (2005) Immunol Rev 204:208-31. It is currently alleged to be the most common neurological disease of young adults, and usually initiates between the ages of 20 and 40, with the tendency to occur in women at almost double the probability in comparison to men.

In MS, the myelin sheath, the material that surrounds and protects the nerve cells and/or their ability to produce is damaged. This is referred to as "demyelization". This damage has the effect of slowing down or blocking messages between the brain and the body, leading to the symptoms observed with MS. Demyelization and scarring or other lesions in areas disseminated in the brain and/or spinal cord are considered characteristic of the disease. Beeton et al. (2007) Journal of Visualized Experiments 594-604.

These lesions appear to alter nerve conduction and induce the disabling neurological deficits that vary with the location of the demyelinated plaques in the CNS. Beeton et al. (2007) Journal of Visualized Experiments 594-604. Its clinical signs and symptoms are variable and depend on the parts of the CNS it affects, and may include motor, sensory, autonomic and cognitive disabilities. Noseworthy et al. (2000) N Engl J Med 343:938-52. Nonetheless, some common symptoms of MS include: (1) overwhelming sense of fatigue; (2) balance—walking and co-ordination difficulties; (3) visual problems—double vision and loss of sight; (4) numbness and tingling in hands and feet; (5) pain—both mild and severe; loss of muscle strength; (6) stiffness and spasms in muscles; (7) mood swings—depression and anxiety; (8) memory and concentration problems; as well as (9) speech problems (The National MS Society Web Site).

Progressive disability is the fate of most patients with MS, especially when a 25-year perspective is included. Half of MS patients require a cane to walk within 15 years of disease onset. MS is a major cause of neurologic disability in young and middle-aged adults and, until the past decade, has had no known beneficial treatments. MS is difficult to diagnose because of the non-specific clinical findings, which led to the development of highly structured diagnostic criteria that include several technological advances, consisting of MRI scans, evoked potentials, and cerebrospinal fluid (CSF) studies. Diagnostic criteria generally rely upon the general principles of scattered lesions in the central white matter occurring at different times and not explained by other etiologies such as infection, vascular disorder, or autoimmune disorder.

MS is widely considered an autoimmune disease whereby an unknown agent or agents triggers a T-cell-mediated inflammatory attack, causing demyelization of CNS (central nervous system) tissue. Weiner et al. (2004) Arch Neurol 61:1613-1615. The evidence for an autoimmune reaction targeting myelin is strong but not definitive. There are, for example, descriptions of primary oligodendrocyte apoptosis with microglial activation in early multiple sclerosis lesions in the absence of lymphocytes or myelin phagocytosis. Manuel et al. (2006) Brain.

MS characteristically is reported as having four patterns of disease: relapsing-remitting MS (RRMS), primary progressive MS (PPMS), progressive relapsing MS (PRMS); and secondary progressive MS (SPMS). An estimated 50% of patients with RRMS will develop SPMS in 10 years, and up to 90% of RRMS patients will eventually develop SPMS. Each pattern of disease may present as mild, moderate or severe. Persons with RRMS present defined attacks of worsening neurologic function. These attacks are followed by partial or complete recovery periods (remissions), during which no disease progression occurs, (about 85% of people are initially diagnosed with RRMS).

PPMS is characterized by slowly worsening neurologic function from the beginning, with no distinct relapses or remissions (about 10% of people are diagnosed with PPMS). In SPMS, following an initial period of RRMS, many people develop a Secondary-Progressive disease course in which the disease worsens more steadily, (about 50% of people with RRMS develop this form of the disease within 10 years). In PRMS people experience steadily worsening disease symptoms from the beginning, but with clear attacks of worsening neurologic function along the way, while the disease appears to progress without remissions (5%) (The National MS Society web site). There is currently no cure for MS although several treatments that attempt to reduce disease activity and disease progression are available.

Six drugs in four classes are approved in the United States for the treatment of MS. FDA-Approved disease treatments include the following: interferon class, IFN-beta-1a (REBIF™ and AVONEX™) and IFN-beta-1b (BETASERON™); glatiramer acetate (COPAXONE™), a polypeptide; natalizumab (TYSABRI™); and mitoxantrone (NOVANTRONE™), a cytotoxic agent. Other drugs have been used with varying degrees of success, including corticosteroids, methotrexate, cyclophosphamide, azathioprine, and intravenous (IV) immunoglobulin. The benefits of currently approved treatments are relatively modest for relapse rate and prevention of disability in MS.

REBIF™ (interferon beta 1a) is a medication manufactured by a biotechnological process that produces the same interferon beta as found in the human body. REBIF™ is reportedly given three times a week subcutaneously. (From the FDA approved prescription information for REBIF™.

AVONEX™ (interferon beta 1a) is a medication manufactured by a biotechnological process that produces the same interferon beta as found in the human body. AVONEX™ is reportedly given as a once a week intramuscular injection. (From the FDA approved prescription information for AVONEX™)

BETASERON™ (interferon beta 1b) is a medication manufactured by a biotechnological process that made up the same interferon beta as found in the human body. BETASERON™ is reportedly injected subcutaneously every other day. (From the FDA approved prescription information for BETASERON™).

COPAXONE™ (glatiramer acetate) is a synthetic protein that simulates myelin basic protein. Through a mechanism that is not completely understood, this drug seems to block myelin damaging T cells by acting as a myelin decoy. COPAXONE™ is reportedly injected subcutaneously once a day. (From the FDA approved prescription information for COPAXONE™).

TYSABRI™ (natalizumab) is a laboratory produced monoclonal antibody. It is designed to hamper movement of potentially damaging immune cells from the bloodstream, across the "blood-brain barrier" into the brain and spinal cord. TYSABRI™ is reportedly given once every four weeks by intravenous infusion. (From the FDA approved prescription information for TYSABRI™).

NOVANTRONE™ (mitoxantrone) belongs to the general group of medicines called antineoplastics. It has been used to treat certain forms of cancer. It reportedly acts in MS treatment by suppressing the activity of T cells, B cells and macrophages that are presumed to lead the attack on the myelin sheath. (From the FDA approved prescription information for NOVANTRONE™).

Current therapies for combating inflammatory diseases generally fail to provide a multi-component approach targeting multiple components of pathogenesis. For example, many treatments for autoimmune diseases involve targeting a single component of a disease, either by blocking cellular proliferation, or by suppressing the immune response in order to block inflammation. Consequently, there is a strong need to provide effective therapeutics which target multiple components of inflammatory disease pathogenesis by targeting and modulating PCK isoform activity. Specifically targeted therapeutics that are capable of selective inhibition or activation of specific PKC isoforms are necessary and would provide for a therapeutic approach that targets multiple components of inflammatory disease pathogenesis, while retaining a low level of side effects, for example, when topically administered. Thus, development of therapeutics that reduce secretion of proinflammatory cytokines and/or regulate immunomodulators via PKC isoform modulation would be beneficial in alleviating topical and systemic inflammation generally, as well as a host of inflammatory and/or autoimmune diseases as discussed herein.

In an experimental model of autoimmune encephalitis (EAE), cavtratin inhibited blood brain barrier disruption, the invasion of CD45+ cells into the brain parenchyma, and ameliorates functional deficits. This data suggest that modulation of caveolar function could be a useful therapeutic approach in multiple sclerosis.

Traumatic Brain Injury (TBI)

Traumatic brain injury (TBI) or neurotrauma contributes to numerous deaths and cases of permanent disability in the United States and world-wide. Of the 1.4 million people who sustain a TBI each year in the United States, 50,000 will die, 235,000 will be hospitalized, and another 1.1 million will be treated and released from an emergency department. Among children ages 0 to 14 years in the United States, TBI results in 435,000 visits to the emergency department each year, 2,685 fatalities, and 37,000 hospitalizations. Langlois se al., Traumatic brain injury in the United States: emergency department visits, hospitalizations, and deaths, Atlanta (Ga.): Centers for Disease Control and Prevention, National Center for Injury Prevention and Control; 2004.

As used herein, a "neurodegenerative event" means stroke, seizure, toxin exposure, ischemia/reperfusion injury, hypoxia, traumatic brain injury, multiple sclerosis, neuromyelitis optica, spinal cord injury, Rett syndrome, Alzheimer's disease, Parkinson's disease, Huntington's disease, dementia (HIV related or not), or other neurodegenerative disorders as well as depression, schizophrenia, obsessive-compulsive disorder, anorexia nervosa and bulimia nervosa and others. The term "neurodegenerative event" is also meant to encompass conditions resulting in significant tissue damage that are or may be associated with damage to nerves in the PNS. Illustrative examples include a topical injury such as a bruise, wound or burn, or nerve damage associated with a cut or surgery.

Due to their inhibiting properties towards proteases, agents of the invention are useful, e.g., in the treatment or prevention of a variety of debilitating psychiatric, psychotic, neurological or vascular states, e.g. of a condition, disease or disorder of the vascular system or of the nervous system, in which beta-amyloid generation or aggregation plays a role, or, based on the inhibition of BACE-2 (beta-site APP-cleaving enzyme 2) or cathepsin D, which are close homologues of the pepsin-type aspartyl proteases and beta-secretase, and the correlation of the BACE-2 or cathepsin D expression with a more tumorigenic or metastatic potential of tumor cells, as anti-cancer medicaments, e.g. in the suppression of the metastasis process associated with tumor cells.

The said condition, disease or disorder of the vascular system or of the nervous system is exemplified by, and includes, without limitation, an anxiety disorder, such as panic disorder with or without agoraphobia, agoraphobia without history of panic disorder, an animal or other specific phobia, including a social phobia, social anxiety disorder, anxiety, obsessive-compulsive disorder, a stress disorder, including post-traumatic or acute stress disorder, or a generalized or substance-induced anxiety disorder; a neurosis; seizures; epilepsy, especially partial seizures, simple, complex or partial seizures evolving to secondarily generalized seizures or generalized seizures [absence (typical or atypical), myoclonic, clonic, tonic, tonic-clonic or atonic seizures]; convulsions; migraine; an affective disorder, including a depressive or bipolar disorder, e.g. single-episode or recurrent major depressive disorder, major depression, a dysthymic disorder, dysthymia, depressive disorder NOS, bipolar I or bipolar II manic disorder or cyclothymic disorder; a psychotic disorder, including schizophrenia or depression; neurodegeneration, e.g. neurodegeneration arising from cerebral ischemia; an acute, traumatic or chronic degenerative process of the nervous system, such as Parkinson's disease, Down's syndrome, dementia, e.g. senile dementia, dementia with Lewy bodies or a fronto-temporal dementia, a cognitive disorder, cognitive impairment, e.g. mild cognitive impairment, memory impairment, an amyloid neuropathy, a peripheral neuropathy, Alzheimer's disease, Gerstmann-Straeussler-Scheinker syndrome, Niemann-Pick disease, e.g. Niemann-Pick type C disease, brain inflammation, a brain, spinal cord or nerve injury, e.g. traumatic brain injury (TBI), a nerve trauma or a brain trauma, vascular amyloidosis, cerebral haemorrhage with amyloidosis, Huntington's chorea, amyotrophic lateral sclerosis, multiple sclerosis, neuromyelitis optica, or fragile X syndrome; scrapie; cerebral amyloid angiopathy; an encephalopathy, e.g. transmissible spongiform encephalopathy; stroke; an attention disorder, e.g. attention deficit hyperactivity disorder; Tourette's syndrome; a speech disorder, including stuttering; a disorder of the circadian rhythm, e.g. in subjects suffering from the effects of jet lag or shift work; pain; nociception; itch; emesis, including acute, delayed or anticipatory emesis, such as emesis induced by chemotherapy or radiation, motion sickness, or post-operative nausea or vomiting; an eating disorder, including anorexia nervosa or bulimia nervosa; premenstrual syndrome; a muscle spasm or spasticity, e.g. in paraplegic patients; a hearing disorder, e.g. tinnitus or age-related hearing impairment; urinary incontinence; glaucoma; inclusion-body myositis; or a substance-related disorder, including substance abuse or dependency, including a substance, such as alcohol, withdrawal disorder. Agents of the invention may also be useful in enhancing cognition, e.g. in a subject suffering from a dementing condition, such as Alzheimer's disease; as premedication prior to anaesthesia or a minor medical intervention, such as endoscopy, including gastric endoscopy; or as ligands, e.g. radioligands or positron emission tomography (PET) ligands.

Inflammatory Bowel Disease (IBD)

In various embodiments, the compositions provided herein are useful for the treatment of an inflammatory bowel disease. In specific embodiments, the inflammatory bowel disease is ulcerative colitis or Crohn's disease.

The intestinal apparatus is affected by many inflammatory diseases generally capped as inflammatory bowel diseases. In particular, Crohn's disease is a severe chronic inflammatory disease affecting various levels of the digestive tract, from the mouth to the anus, particularly it can be observed in the last portion of the small intestine, either the ileum, the colon or both and sometimes in the mucous membrane of the colon and in the anal region as well.

In the interested intestinal part, inflammation, swelling and ulceration occur in the whole intestinal wall causing stenosis, bleeding ulcers and pain, while the non-affected tissue portions appear normal. Crohn's disease exhibits alternate periods of inflammatory symptoms of variable gravity with symptoms such as: diarrhea, abdominal pain, and weight loss. From two-thirds to three-quarters of patients with Crohn's disease require surgery at some point in their lives. Surgery is used either to relieve symptoms that do not respond to medical therapy or to correct complications such as blockage, perforation, abscess, or bleeding in the intestine.

Combination Therapies

The compositions useful within the present invention are intended to be useful in the methods of present invention in combination with one or more additional compounds useful for treating the diseases or disorders contemplated within the invention. These additional compounds may comprise compounds of the present invention or compounds, e.g., commercially available compounds, known to treat, prevent, or reduce the symptoms of the diseases or disorders contemplated within the invention.

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the patient either prior to or after the onset of a disease or disorder. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions useful within the present invention to a patient, preferably a mammal, more preferably a human, may be carried out using known procedures, at dosages and for periods of time effective to treat a disease or disorder in the patient. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder in the patient.

Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder in a patient.

In one embodiment, the compositions useful within the invention are formulated using one or more pharmaceutically acceptable excipients or carriers. In one embodiment, the pharmaceutical compositions of the invention comprise a therapeutically effective amount of a compound useful within the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, and thimerosal. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In one embodiment, the compositions useful within the invention are administered to the patient in dosages that range from one to five times per day or more. In another embodiment, the compositions useful within the invention are administered to the patient in range of dosages that include, but are not limited to, once every day, every two, days, every three days to once a week, and once every two weeks. It will be readily apparent to one skilled in the art that the frequency of administration of the various combination compositions useful within the invention will vary from individual to individual depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physical taking all other factors about the patient into account.

Compounds for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments there between.

In some embodiments, the dose of a compound is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating a disease or disorder) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other cognition improving agents.

The term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a disease or disorder in a patient.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e., having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e., drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds of the invention, and a further layer providing for the immediate release of a medication for treatment of a disease or disorder. Using a wax/pH-sensitive polymer mix, a gastric insoluble composition may be obtained in which the active ingredient is entrapped, ensuring its delayed release.

Parenteral Administration

For parenteral administration, the compounds may be formulated for injection or infusion, for example, intravenous, intramuscular or subcutaneous injection or infusion, or for administration in a bolus dose and/or continuous infusion. Solutions, suspensions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 2003/0147952, 2003/0104062, 2003/0104053, 2003/0044466, 2003/0039688, and 2002/0051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In a preferred embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound will depend on the age, sex and weight of the patient, the current medical condition of the patient and the progression of disease/disorder in the patient being treated. The skilled artisan will be able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Example 1: Cell Isolation and Culture

Cultured rat heart microvascular endothelial cells (RHMVEC) were purchased from VEC Technologies (Rensselaer, N.Y.) and grown on fibronectin coated plates in MCDB-131 complete medium (VEC Technologies). BAEC were isolated from bovine aortas obtained from a local slaughter house and grown in DMEM (high glucose; Cellgro) supplemented with 10% FBS (Hyclone) and pen/strep. Human Umbilical Vascular Endothelial Cells (HUVEC) were isolated locally from human umbilical cords and grown in M199 medium (Invitrogen) supplemented with endothelial cell growth supplement (Invitrogen), 10% FBS, L-glutamine (Invitrogen) and pen/strep.

Example 2: T7 Phage Library Construction

Novagen T7select phage display system was used for the random screening of peptides that facilitate endothelial cell uptake in conjunction with a pool of oligonucleotides randomly coding for 7-mer peptides. The 7-mer random peptide primers containing HindIII/XhoI sites were designed as follows:

```
Sense primer:
                                         (SEQ ID NO. 9)
5'-GCTAGAATTCNNNBNNBNNBNNBNNBNNBNNBAAGCTTACTGCAGTA GCATG-3',
wherein N = A, T, C, G; and B = G, C, T;
```

-continued

Anti-sense primer:
(SEQ ID NO. 10)
5'-CATGCTACTGCAGTAAGCTT-3'.

Similar amount of each primer were mixed and annealed at 95° C. for 5 minutes, then cooled down to room temperature. Fill-in reactions were then performed by using the Klenow enzyme to generate blunt ends DNA fragments. After HindIII/XhoI digestion, 0.06 pmol of inserts were ligated into T7select415-1b vector. The ligation reaction was added directly to T7 packaging extracts for in vitro packaging, and a $3\times10^7$ pfu of phage library was generated.

For amplification, the library was inoculated with BL21 culture ($OD_{600}$ of 0.5-1.0) and induced with 1 mM IPTG at 37° C. for 2 hours until cell lysis was observed. The lysate containing phages was clarified by centrifugation at 8000×g for 10 min, the supernatant was titered and aliquots were stored a 4° C.

Example 3: Phage Selection by Endocytosis in EC and Amplification

Rat heart microvascular endothelial cells (RHMVEC) (80% confluent; approximately $2\times10^7$ cells/100 mm dish) were washed with a phosphate buffer solution (PBS) and pre-incubated in serum-free medium at 37° C. for 30 minutes and inoculated with an extract ($5\times10^9$ pfu) of the T7 phage library to reach a multiplicity of infection (MOI) of 250. After incubation for 1 hour at 37° C., cells were washed with ice-cold PBS and acid washed with 0.1N HCl, pH 2.2, for 15 seconds to remove unbounded and weakly associated phages from the cell surface.

Cells were then trypsinized, centrifuged and lysed with sterile deionized water on ice. Cell debris were removed by centrifugation and the supernatant containing previously internalized phages were amplified as described above and titered between each round to ensure that $5\times10^9$ pfu of input phages was used at the start of each successive round. After completion of six rounds of selection/amplification, Eshcherichia Coli BL21 was infected with the resulting phages and plated, individual plaques were picked, amplified and sequenced.

Example 4: Peptide Synthesis

Peptides, corresponding to Endo5 (RRPPR) (SEQ ID NO. 1) or Antennapedia (RQIKIWFQNRRMKWKK) (SEQ ID NO. 2) with or without cargo fused to their C-terminus end (DGIWKASFTTFTVTKYWFYR) (SEQ ID NO. 5) were synthesized by standard Fmoc chemistry and analyzed by mass spectrometry to confirm purity by the W.M. Keck biotechnology resource center at Yale University School of Medicine. Fluorophores (carboxyfluorescein for Endo5 and rhodamine for AP) were added to the N-terminus following synthesis.

Before each experiment, desiccated peptides were weighed, dissolved in dimethyl sulfoxide (DMSO; J. T. Baker, Philipsburg, N.J.) to $5\times10^{-2}$-$10^{-2}$ M and diluted to $10^{-3}$ M with distilled water.

Example 5: NO Release

VEGF-induced NO release experiments were performed as previously described.

Briefly, confluent BAEC were incubated in serum-free DMEM for 6 hours with peptides. Media was removed and fresh serum-free DMEM was added, with or without VEGF ($10^{-9}$ M) for 30 minutes. Media was collected, cells were trypsinized and counted, and nitrites levels in the supernatant were determined by using a Sievers NO chemiluminescence analyzer.

Example 6: Modified Miles Assay

Plasma leakage in mouse skin was studied using the Miles assay as previously described. Briefly, male Swiss mice (30-35 g) were anesthetized and injected with Evans blue (30 mg/kg in PBS; Sigma). Phenylisothiocyanate (5% in mineral oil), an analog of mustard oil (Pierce, Rockford, Ill.) was applied on the right ear with a cotton tip.

The left ear was used as a control and was treated with mineral oil alone. After 30 minutes, the anesthetized animals were sacrificed, perfused, ears were removed, dried and weighed. Evans blue was extracted from the ears with formamide and quantified spectrophotometrically at 595 nm.

Example 7: Quantification of Internalization

Cultured BAEC were grown in 6-well plates until confluence was reached. Cells were washed and incubated in 1 mL of DMEM containing labeled peptides ($10^{-6}$ M) for 1, 2, 4 or 6 hours at 37° C., washed three times with cold PBS containing 0.1 M glycine (pH 4) to remove non-specific surface staining.

After complete media removal, cells were trypsinized, centrifuged and proteins were extracted by adding 150 µL of SDS-based or Triton X-100 lysis buffer. Membranes were removed by centrifugation, and internalized peptides were quantified by using a fluorescence plate reader (Perseptive Biosystems).

Cells incubated with peptides for 5 minutes and washed as described were used as basal surface staining. Linearity of both fluorophores used was determined by performing a concentration-fluorescence curve using lysis solution. Experiments with each fluorophore were performed individually to prevent cross-interference.

Example 8: CPP Imaging of Live Human Umbilical Vascular Endothelial Cell (HUVEC)

Freshly isolated HUVEC were grown in M199 media supplemented with glutamine, 10% FBS and endothelial cell growth supplement on Petri dishes with glass bottom. Since CPPs bind non-specifically to glass, the background fluorescence was reduced by pretreating glass-bottom Petri dishes with a blocking solution containing unlabelled AP and Endo5 for 30 minutes ($5\times10^{-5}$ M) in colorless M199 media with 1% FBS.

After cell seeding, media was removed and carboxyfluorescin-labeled Endo5 and Rhodamine-labeled AP were added to cells ($10^{-5}$M) and cells were incubated at 37° C. and 5% $CO_2$ for 1 hour (pulse). Media was removed, cells were rinsed once with warm culture media and peptide uptake was rapidly visualized on a Zess Axiovert inverted fluorescence microscope by performing a Z-stack of captured images followed by volume deconvolution (Openlab software). The new media was left on cells for an additional 2 hours (total 3 hours) to chase CPP localization, and cells were visualized again (chase).

Example 9: Screening of Phage Library for Peptides that Mediate Phage Internalization A T7 phage display library that expresses on average 0.1-1 copy of randomly generated 7-mer peptides on the capsid was generated. A constant amount of input phages ($5 \times 10^9$) was added to cultured rat heart microvascular endothelial cells (RHMVEC) and these phages were selected for their capacity to get quickly internalized (cellular uptake) by the cell monolayer.

The RHMVEC were incubated for 1 hour with $5.0 \times 10^9$ phages (input), lysed, and recovered phages were quantified (cell uptake) and amplified for the next round of biopanning. Recovery percentage is expressed as the ratio of recovered phages to input phages. As shown in Table 1, after six rounds of infection/purification, a 100-fold increase in the percentage of recovered phages was observed, from 0.018 (round 1) to 1.8% (round 6) under identical starting conditions, providing evidence that the resulting phage library displays enhanced endothelial cell internalization properties. 24 individual phages were isolated.

TABLE 1

| Round | Input phages (supernatant) | Recovered phages (cell uptake) | Recovery % |
|---|---|---|---|
| 1 | $5.0 \times 10^9$ | $9.4 \times 10^5$ | 0.018 |
| 2 | $5.0 \times 10^9$ | $3.8 \times 10^6$ | 0.076 |
| 3 | $5.0 \times 10^9$ | $7.5 \times 10^6$ | 0.15 |
| 4 | $5.0 \times 10^9$ | $2.8 \times 10^7$ | 0.56 |
| 5 | $5.0 \times 10^9$ | $4.5 \times 10^7$ | 0.90 |
| 6 | $5.0 \times 10^9$ | $9.0 \times 10^7$ | 1.8 |

As shown in FIG. 1, analysis of the phage library's capacity of internalization in endothelial cells after each round of selection suggests an exponential increase in the uptake percentage ($R^2=0.975$ for correlation with exponential function).

Following completion of biopanning and enrichment, the resulting phages were plated, and individual plaques were amplified and sequenced. Out of the 24 individual phages isolated, five phages were coding for the unexpectedly short 5-mer peptide RRPPR (SEQ ID NO. 1), termed Endo5, which was the most frequently identified peptide (21%).

Codon analysis of the DNA sequence of Endo5 coding phage revealed the random and unexpected insertion of a stop codon in the coding sequence (CGGCGCCCGC-CTCGT<u>TGA</u>GGG) (SEQ ID NO. 8), which rationalized the smaller size of Endo5 compared to the theoretical 7 amino acid CPP size this approach can generate.

Example 10: eNOS Inhibitory Activity

AP-Cav blocks agonist-induced eNOS activity in cultured endothelial cells (Bucci et al., 2000, Nat. Med. 6:1362-7), and this biological activity is dependent on AP-Cav's internalization, dosage and pretreatment time. In the study described herein, the uptake potential of Endo5 was compared with that of AP by testing the effect of Endo5 fused to Cav (endo5-Cav) on NO release by cultured BAEC.

FIGS. 2A-2D provide bar graphs demonstrating that Endo5-Cav (SEQ ID NO. 1/SEQ ID NO. 5) is more potent than AP-Cav (SEQ ID NO. 2/SEQ ID NO. 5) at blocking VEGF-induced NO release. Referring to FIG. 2A, a six-hour pretreatment of BAEC with AP or Endo5 without cargo, or with AP-Cav or Endo5-Cav ($10^{-5}$M) had no significant effect on basal (unstimulated) NO release as assayed by NO-specific chemiluminescence. Similar pretreatment with AP or Endo5 showed no significant effect on VEGF-induced NO release, whereas pretreatment with AP-Cav ($10^{-5}$M) blocked VEGF activity by 48% (Bucci et al., 2000, Nat. Med. 6:1362-7). Interestingly, similar pretreatment with Endo5-Cav ($10^{-5}$M) completely impaired VEGF activity on BAEC NO release, providing evidence that Endo5-mediated uptake was more efficient than that of AP.

The pharmacological effect of Endo5-Cav on VEGF-induced NO release was further studied by performing dose-dependent inhibition experiments. As indicated by FIG. 2B, pretreatment with Endo5-Cav ($10^{-6}$-$10^{-5}$ M) caused a dose-dependent inhibition of VEGF-induced NO release with a near-maximum effect at $10^{-5}$ M. AP-Cav activity reached maximum inhibition at $2.5 \times 10^{-5}$M due to peptide insolubility at greater dose but displayed a much weaker inhibitory activity (61% inhibition). Analysis of dose response curves followed by non-linear regression (curve fit) revealed that the $EC_{50}$ of AP-Cav and Endo5-Cav were $1.8 \times 10^{-6}$ and $7.5 \times 10^{-6}$ M, respectively.

Since the inhibition of Endo5-Cav on VEGF-induced eNOS activity was more robust than that of AP-Cav at a similar concentration, a time-dependent comparison between AP-Cav and Endo5-Cav effect on eNOS activity was performed. As shown by FIG. 2C, AP-Cav ($10^{-5}$ M) had a time-dependent effect on VEGF-induced NO release in BAEC although a minor difference is observed between 4 h and 6 h incubation time points (57% vs 49%, respectively), suggesting that a near-complete equilibrium between AP-Cav uptake and intracellular degradation/elimination may be reached.

Endo5-Cav inhibitory effect was also time-dependent but more robust, with a complete eNOS inhibition at 4 hours, suggesting a faster internalization of Endo5. Moreover, the data indicated that a six-hour pretreatment with AP-Cav ($10^{-5}$ M) had a similar effect on VEGF-induced NO release as compared to a two-hour pretreatment with Endo5-Cav at a similar concentration, which provided evidence that the rate of uptake Endo5-Cav was approximately three times that of AP-Cav, as indicated by FIG. 2C.

The Cav AB domain (amino acids 82-95 of human caveolin-1; SEQ ID NO. 6) mediates eNOS inhibition. Bernatchez et al., 2005, Proc. Natl. Acad. Sci. 102:761-66. Because Endo5 appears more potent that AP at promoting cargo internalization, both AP-Cav leader and cargo sequences were modified in order to maximize the therapeutic effect/size ratio compared to AP-Cay. Hence, Endo5-CavAB (a 19-mer peptide) was synthesized and its activity was compared to that of AP-Cav (a 36-mer acid peptide).

FIG. 2D shows that pretreatment of BAEC for six hours with Endo5-CavAB ($10^{-5}$ M) completely blocked VEGF-induced NO release, whereas AP-Cav inhibited VEGF effect by only 52% at a similar dose. Interestingly, pretreatment with Endo5-CavAB ($2 \times 10^{-6}$ M) had a similar effect as AP-Cav ($10^{-5}$ M), inhibiting VEGF-induced NO release by 49%.

Taken together, this data suggest the feasibility of optimizing both AP-Cav cell uptake sequence and cargo to maximize the therapeutic potential per molecule or per amino acid.

Example 11: Anti-Inflammatory Properties

EC-derived NO production plays an active role in inflammation, in part by promoting increase in intra-capillary pressure and subsequent vascular permeability. Pretreatment of mice with AP-Cav blocks vascular leakage in the Miles assay (Bucci et al., 2000, Nat. Med. 6:1362-7; Bernatchez et al., 2005, Proc. Natl. Acad. Sci. USA 102:761-6). This established model may thus be a valuable tool to assess the in vivo potency of Endo5-fused peptides. FIGS. 3A and 3B demonstrate that Endo5-Cav (SEQ ID NO. 1/SEQ ID NO. 5) blocks Evans blue extravasation in vivo.

Referring to FIG. 3A, a one-hour pretreatment of mice with AP-Cav (1 mg/kg) attenuated by 37% (n=6 per group) compared to mice treated with AP alone (similar dose on a molecular weight basis). Endo5-Cav inhibited mustard oil-induced vascular leakage by 58% compared with Endo5 pretreatment alone (n=6 or 8 per group) and showed a statistically significant greater inhibitory activity than AP-Cav (†P<0.05).

The plot shown in FIG. 3B indicates that both AP-Cav and Endo5-Cav attenuate Evans blue extravasation in the ear skin and tissue compared to control peptides, although Endo5-Cav was more potent. Without intending to be limited by any theory, the incomplete inhibition displayed by Endo5-Cav on mustard oil-induced inflammation may be explained by the observation that NO plays only a partial role in mediating vascular permeability in this model (Bucci et al., 2000, Nat. Med. 6:1362-7).

Example 12: Internalization by Endothelial Cells

AP is a CPP that crosses the membrane of neurons. Joliot et al., 1991, Proc. Natl. Acad. Sci. USA 88:1864-8. As discussed elsewhere herein, Endo5 was unexpectedly found to promote high internalization of phages in endothelial cells, and Endo5-Cav was unexpectedly found to be more potent that AP-Cav at preventing eNOS activation and vascular permeability.

In the study described herein, the internalization rate of Endo5 was directly compared to that of AP by using carboxyfluorescein and rhodamine-labelled form of each peptide, respectively. The linearity of each fluorophore-coupled peptide was confirmed by performing a standard concentration/fluorescence curve.

FIGS. 4A-4B are graphs illustrating the finding that Endo5 (SEQ ID NO. 1) is internalized faster than AP (SEQ ID NO. 2) in cultured endothelial cells. Referring to FIG. 4A, calibration was performed in order to obtain similar absorbance values for both fluorophores (by adjusting gain settings for each fluorophores. BAEC were incubated separately with fluorophore-labelled peptides ($10^{-6}$ M) for 1, 2, 4 or 6 hours, acid washed, lysed, and total peptide uptake was determined by quantifying fluorescence.

A linear increase in AP internalization with time was observed, as indicated by FIG. 4B, peaking at 6 hours at a value of $1.07 \times 10^{-9}$ moles of AP/$10^6$ cells. This indicates that approximately 11% of the total amount of rhodamine-AP added at time zero is internalized by a confluent BAEC monolayer in the settings, providing evidence for an active concentration mechanism. The rate of internalization of carboxyfluorescein-Endo5 was greater than that of AP, also peaking at 6 hours with a value of $2.85 \times 10^{-9}$ moles of Endo5/$10^6$ cells, suggesting that 30.5% of the added peptide was internalized after 6 hours, as indicated by FIG. 4B.

Example 13: Internalization in Live Endothelial Cells

In prior studies that attempted to shed light on the uptake mechanisms involved in CPP entry into cells, imaging was performed in fixed cells. The results of these studies may not be reliable in view of the mounting evidence that cell fixation leads to the unexpected nuclear translocation of CPP. Richard et al., 2003, J. Biol. Chem. 278:585-90.

In the present study, epifluorescence microscopy experiments were performed in live HUVEC to compare the uptake mechanism of Endo5 to AP. After blocking glass bottom Petri dishes with unlabeled AP and Endo5 to minimize non-specific binding of labeled peptides, freshly isolated HUVEC were grown to 50% confluent and labeled with a "pulse" of carboxyfluorescein-Endo5 and rhodamine-AP ($10^{-6}$M) for 1 h, rinsed, followed by a two-hour "chase" for a total of 3 hours.

Deconvoluted images were captured after the "pulse" and "chase" periods. FIGS. 5A-5C illustrate that internalization of Endo5 (SEQ ID NO. 1) and AP (SEQ ID NO. 2) uses overlapping cellular pathways in endothelial cells. Both Endo5 (green channel, left) and AP (red channel, center) display diffuse punctate cytoplasmic staining in live HUVEC after 1 h of incubation at 37° C. (FIG. 5A). Nuclear staining was nearly completely absent (dark central area). Interestingly, merged images revealed a high degree of co-localization between Endo5 and AP (FIG. 5A, right). This observation suggests similarity between Endo5 and AP early internalization pathways. Individual incubation of HUVEC with rhodamine-AP caused little or no signal in the carboxyfluorescein-Endo5 channel and vice-versa, suggesting the absence of significant bleed-through.

After a two-hour "chase" period in absence of CPP, the punctate staining for both Endo5 and AP was still noticeable but it displayed a more concentrated rather than diffuse pattern, stressing an active intracellular concentration/localization mechanism (FIG. 5B, left). Merged images (right panel) again revealed co-localization between Endo5 and AP during this long-term phase of intracellular peptide concentration (chase) after initial internalization from the cell surface. Representative cells were shown. Taken together, these data illustrated the similarity of the internalization and intracellular distribution between Endo5 and AP.

The similarity of the internalization pathways between Endo5 and AP was confirmed by performing competition studies and quantifying Endo5 and AP ability to promote cargo entry into cells. Referring to FIG. 5C, AP-Cav ($10^{-5}$ M) partial effect on VEGF-induced NO release was blocked by pretreatment with either AP or Endo5 ($5 \times 10^{-5}$ M). The near-complete inhibition of VEGF-induced NO release mediated by Endo5-Cav was partially prevented by pretreatment with either AP or Endo5 ($5 \times 10^{-5}$ M)

As shown by FIG. 5C, the 91% inhibition of VEGF-induced NO release by Endo5-Cav was prevented by AP (30% inhibition) or Endo5 (13% inhibition). Taken together, these results suggest that AP and Endo5 are internalized through similar pathways in EC.

Example 14: Treatment of Uveitis

Analysis of Cavtratin on intravitreal injection in the rat model of laser induced neovascularization. In this model, Cavtratin was administered twice at 4 day intervals with the evaluation at day 8. Results from this study are provided in FIG. 6.

B10.RIII animals (Jackson Laboratories) are immunized with human IRBP$_{161-180}$ peptide at day 0 and treated with the experimental drug via intraperitoneal (ip) injection of peptides formulated in saline daily from days 7-19. On day 19, the peak of inflammation by histopathologicial scoring, animals are sacrificed and eyes fixed and processed for Hematoxylin-and-Eosin (H&E) staining. The degree of EAU is evaluated by histopathological scoring of the retina, and the retinal sections are evaluated in a masked fashion by experienced graders.

Animals are treated in groups of 6, with both eyes processed for histopathology and scored for an n of 12 eyes per group. This number of animals/eyes gives a statistical power to detect a difference between the experimental group and untreated control when the experimental group's histopathologic score is half the value of the control group (intermediate between the untreated control and unimmunized animals). An initial group of animals is graded to confirm variance and validate the sample sizes.

Cohorts of animals are then treated/evaluated to enable the following comparisons:

(1) Treatment with Cavtratin (2.5 mg/kg) vs. untreated control. This confirms that inhibition of caveolin function ameliorates inflammation. The treatment is deemed successful if there is a difference between the histopathological scores of the two groups. If there is a large difference between groups that is not statistically significant, increasing the number to achieve significance is considered. If there is a difference of at least 25% between the mean values but not a statistical significance, the experiment is repeated with higher doses of cavtratin.

(2) Treatment with Endo5-CavAB (SEQ ID NO. 1/SEQ ID NO. 6) (dose response curve, using 0.3, 1.0, and 3.0 mg/kg doses) vs. untreated control. If the 0.3 mg/kg dose produces and effect that is not statistically different from the unimmunized control, lower doses are used, in the order of 0.1, 0.03, 0.01 mg/kg until the effect level is different from the unimmunized control animal score. The study is complete when the dose of Endo5-CavAB (SEQ ID NO. 1/SEQ ID NO. 6) producing the maximal effect is identified.

(3) Treatment with the optimal dose of Endo5-CavAB (SEQ ID NO. 1/SEQ ID NO. 6) vs. a control peptide containing only the cell penetrating fragment of the peptide. This group serves to confirm dose response experiments. Once the optimal dose of Endo5-CavAB (SEQ ID NO. 1/SEQ ID NO. 6) is identified, a comparison of optimal dose Endo5-CavAB (SEQ ID NO. 1/SEQ ID NO. 6) to Cavtratin to the untreated control is made. This last comparison is repeated with fixation for immunohistochemistry and the eyes stained with anti-mouse CD45 and the invasion of the retina with CD45+ cells quantitated.

To establish that modulation of caveolar function ameliorates EAU when administered intravitreally, a rabbit EIU model is used. This EIU model causes both anterior chamber inflammation and retinal damage, and can be scored for retinal histopathology similar to a mouse EAU model.

Before testing Endo5-CavAB (SEQ ID NO. 1/SEQ ID NO. 6) in the rabbit model, an evaluation of potential ocular and retinal toxicity by IVT administration is performed. The lowest dose is chosen as equivalent to the optimal concentration identified in the mouse assuming free distribution within the mouse and free distribution within the rabbit eye.

This dose and doses 10 and 30 fold more are injected intravitreally into rabbits and the retinas removed, fixed and processed for H&E. Both acute studies (retinas taken 24 hours post a single IVT administration) and chronic studies (animals injected daily for 7 days) are performed. To conserve animals, two animals (four eyes) are evaluated per group (12 animals total). Retinal sections are evaluated by an experienced retinal histopathologist.

Endo5-CavAB (SEQ ID NO. 1/SEQ ID NO. 6) is determined to be non-toxic if there is a lack of observable effect at the optimal dose and if possible the identification of a no observable adverse effect level (NOAEL) and definition of the observed adverse effect at high doses. If the highest dose tested is NOAEL, higher doses are not tested.

Endo5-CavAB (SEQ ID NO. 1/SEQ ID NO. 6) ability to inhibit inhibits retinal inflammation is demonstrated using the following experimental procedure. For the EIU experiments, the Endo5-CavAB (SEQ ID NO. 1/SEQ ID NO. 6) injected does is chosen based on the mouse EAU dose-response curve combined with the toxicity and pharmacokinetics experiments. The target concentration of drug in the vitreous is the concentration achieved in the mouse EAU experiment (assuming free distribution in the mouse) at dosing using the lowest fully effective dose of Endo5-CavAB (SEQ ID NO. 1/SEQ ID NO. 6). The vitreous dose is adjusted using the pharmacokinetic data to achieve the target concentration but not a toxic concentration, and the interval between doses is adjusted.

The vitreous dose and interval chosen is one that provides continuous vitreous concentrations above the target concentration but does not reach the toxic concentration.

Endo5-CavAB (SEQ ID NO. 1/SEQ ID NO. 6) is administered starting on the day of uveitis induction and as dictated by the above until day 6 post-induction. On day 6 animals are sacrificed and eyes processed for histopathological analysis. Sections are evaluated in a masked fashion by experienced graders. This experiment is done with cohorts of 6 animals each with uveitis induced unilaterally by intravitreal injection of antigen.

Animals/eyes with uveitis and sham intravitreal administration of drug are compared to animals that received Endo5-CavAB (SEQ ID NO. 1/SEQ ID NO. 6). This experiment is repeated twice.

Rabbit Model Experiments:

Rabbit toxicology. The objective of this series is to ensure that the drug itself is not producing any toxic effects in the animals that might interfere with the uveitis model. A secondary objective would be to establish that higher doses than we are using do not have a toxic effect and that there is a therapeutic window.

3 doses of the drug in the concentration intended for use and 3 fold higher and 10 fold higher are tested. Each animal is injected in only one eye with drug. Two injections of drug are performed minoring the intended administration in the efficacy studies; the first injection at day 0 and the second at day 3. For each dose, two time points are evaluated, day 4 (one day after the second injection) and day 6 (3 days after the second injection). All animals are clinically examined on days 1, 3 (prior to the second injection), 4 (for the animals to be sacrificed at 4 days) and 6. Following clinical examination, blood is taken and stored for later PK analysis, and the animals will be sacrificed and eyes fixed and processed for histopathology. All treated eyes are sectioned and stained (H&E) and tissues (including anterior segment and retina) examined by an experienced ocular histopathologist.

Efficacy Testing

The uveitis model is conducted per existing protocols in the Rosenbaum/Lin lab. Only one eye is injected with immunogen to induce the uveitis and only that eye is injected with drug. At least two doses of the drug are tested intravitreally. At each dose, the drug is administered at day 0 and day 3 with sacrifice at day 6. Endpoints (primary) are cells and protein in the aqueous with clinical scoring as a secondary. Cells are counted either using a cell counter (Coulter counter) or using a hemocytometer.

A final clinical exam is performed on Day 6, a sample of blood is taken for storage for later PK, and the animal sacrifice. The experimental eye is taken for analysis. All treated eyes are sectioned and stained (H&E) and tissues (including anterior segment and retina) examined by an experienced ocular histopathologist.

Animals are tested in groups of 6 per dose and sacrificed for analysis at a single time point. Given a control group, a cavtratin group and two doses of Endo5-CavAB (SEQ ID NO. 1/SEQ ID NO. 6) and at least one confirmatory group, a minimum of 30 animals os needed for this phase with 30 eyes sectioned, stained and evaluated.

Example 15: Treatment of Traumatic Brain Injury (TBI)

Traumatic brain injury, including both penetrating and closed head injuries as well as injuries to the spinal cord, have long been recognized to have an inflammatory component. See, e.g., Hernandez-Ontiveros D G, Tajiri N, Acosta S, Giunta B, Tan J, Borlongan C V. Microglia activation as a biomarker for traumatic brain injury. Frontiers in neurology. 2013; 4:30 doi: 10.3389/fneur.2013.00030. PubMed PMID: 23531681; PubMed Central PMCID: PMC3607801.

Caveolin and analogs have the ability to decrease the edema and the infiltration of inflammatory cells, and may also suppress microglia/macrophage activation. The effects of caveolin analogs can be demonstrated in a model of closed head injury. The controlled cortical impact model has been shown to result in inflammatory effects both short and long term. See, Acosta S A, et al. Long-term upregulation of inflammation and suppression of cell proliferation in the brain of adult rats exposed to traumatic brain injury using the controlled cortical impact model. PloS one. 2013; 8(1): e53376. doi: 10.1371/journal.pone.0053376. PubMed PMID: 23301065; PubMed Central PMCID: PMC3536766.

Sprague Dawley rats (10 week old) are anesthetized using 1-2% isoflurane and fixed in a stereotactic frame. The skull is surgically exposed and a craniectomy 2.5 mm in radius is made centered on coordinates −0.2 mm anterior and +0.2 mm lateral to midlineat the fronto-parietal cortex. A controlled cortical impactor (Pittsburgh Precision Instruments, Inc., Pittsburgh, Pa.) is used to deliver an impact using a velocity of 6.0 m/s and depth of 1.0 mm below the dura mater and duration of impact of 150 ms. The impactor is angled to impact the skull perpendicular to the brain at the point of impact. Animals are maintained at normal body temperature throughout the procedure. Following the impact, the incision is sutured and the animals are allowed to recover.

Neurological deficits are scored using the system of Clark assessed 24 and 48 hours post injury. See, Clark W et al., Citicoline treatment for experimental intracerebral hemorrhage in mice. Stroke; a journal of cerebral circulation. 1998; 29(10):2136-40. PubMed PMID: 9756595.

Treatment of rats with 2.5 mg/kg cavtratin i.p. immediately after TBI and at 24 hours post TBI reduces the observed neurological deficits. At 48 hours post TBI, rats are sacrificed and the brains sectioned and tissue processed for immunohistochemistry. In untreated animals, the expression of GFAP in the lesion penumbra is dramatically increased, and treatment with cavtratin reduces GFAP expression. See, Glushakov et al., Prostaglandin F2alpha FP receptor antagonist improves outcomes after experimental traumatic brain injury, Journal of neuroinflammation. 2013; 10(1):132. doi: 10.1186/1742-2094-10-132. PubMed PMID:24172576.

Example 16: Treatment of Inflammatory Bowel Disease (IBD)

Inflammatory bowel disease (IBD) including Crohn's disease and ulcerative colitis are inflammatory diseases of the intestinal tract. There are many models of IBD and the most popular is the dextran sulfate sodium model. See, e.g., Koboziev et al., Pharmacological intervention studies using mouse models of the inflammatory bowel diseases: translating preclinical data into new drug therapies, Inflammatory bowel diseases. 2011; 17(5):1229-45. doi: 10.1002/ibd.21557. PubMed PMID: 21312318; PubMed Central PMCID: PMC307537. This model is used to demonstrate the efficacy of caveolin analogs.

C57B1/6 mice are fed dextran sulfate sodium 2% in the drinking water for 9 days. Body weights are measured daily. At the end of 9 days, mice are sacrificed and the first distal centimeter of the colon subject to histopathological analysis. Sections are scored according to the scoring system described in Jirkof et al., Burrowing is a sensitive behavioral assay for monitoring general wellbeing during dextran sulfate sodium colitis in laboratory mice. Laboratory animals. 2013, 47(4):274-83. doi: 10.1177/0023677213493409. PubMed PMID:23828853.

Treatment of these mice with 2.5 mg/kg cavtratin or Endo-5 CavAB (or other caveolin analog) i.p. daily beginning at day 1 will reduce the weight loss at 9 days and improve the histopathologic sore.

Example 17: Treatment of Multiple Sclerosis (MS)

Multiple Sclerosis has long been recognized as an inflammatory condition and current treatments include immunosuppressants such as steroids, methotrexate, and interferons (Betaseron®, Avonex®, etc.) and more recently Gilenya® (Fingolimod).

Patients diagnosed with MS, including relapsing remitting and primary progressive types, are treated with Endo-5 CavAB (SEQ ID NO.1/SEQ ID NO. 6) (or other caveolin analog) at 80 mg per day by subcutaneous injection. This treatment improves the symptoms of MS, including improved motor function, gait, etc. The changes in the patient receiving the treatment are measured using the Multiple Sclerosis Functional Composite. See, e.g., the website of the National MS Society: Clinical Study Measures.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for treating an inflammatory disease or condition in a subject in need thereof comprising administering a composition comprising a transport construct, wherein the transport construct comprises a transport peptide of the amino acid sequence RRPPR (SEQ ID NO: 1) that is linked to a cargo moiety comprising a peptide of amino acid sequence selected from the group consisting of SEQ ID NOS: 3-6.

2. The method of claim 1, wherein the inflammatory disease or condition is uveitis, multiple sclerosis, neuromyelitis optica, traumatic brain injury or inflammatory bowel disease.

3. The method of claim 1, wherein the composition is administered by at least one route selected from the group consisting of intravenous, oral, inhalational, rectal, vaginal, transdermal, intranasal, buccal, sublingual, parenteral, intrathecal, intragastrical, ophthalmic, pulmonary and topical.

4. The method of claim 1, wherein the transport construct of the composition is selected from the group consisting of: SEQ ID NO:1-SEQ ID NO:3; SEQ ID NO:1-SEQ ID NO:4; SEQ ID NO:1-SEQ ID NO:5; SEQ ID NO:1-SEQ ID NO:6; SEQ ID NO:3-SEQ ID NO:1; SEQ ID NO:4-SEQ ID NO:1; SEQ ID NO:5-SEQ ID NO:1; and SEQ ID NO:6-SEQ ID NO:1.

5. The method of claim 2, wherein the transport construct of the composition is selected from the group consisting of: SEQ ID NO:1-SEQ ID NO:3; SEQ ID NO:1-SEQ ID NO:4; SEQ ID NO:1-SEQ ID NO:5; SEQ ID NO:1-SEQ ID NO:6; SEQ ID NO:3-SEQ ID NO:1; SEQ ID NO:4-SEQ ID NO:1; SEQ ID NO:5-SEQ ID NO:1; and SEQ ID NO:6-SEQ ID NO:1.

6. The method of claim 3, wherein the transport construct of the composition is selected from the group consisting of: SEQ ID NO:1-SEQ ID NO:3; SEQ ID NO:1-SEQ ID NO:4; SEQ ID NO:1-SEQ ID NO:5; SEQ ID NO:1-SEQ ID NO:6; SEQ ID NO:3-SEQ ID NO:1; SEQ ID NO:4-SEQ ID NO:1; SEQ ID NO:5-SEQ ID NO:1; and SEQ ID NO:6-SEQ ID NO:1.

* * * * *

SEQUENCE LISTING

<160> NUMBER OF SEQ ID NOS: 23

<210> SEQ ID NO 1

```
<211> LENGTH: 5
<212> TYPE: PRT
<213> ORGANISM: Artificial
<220> FEATURE:
<223> OTHER INFORMATION: Synthesized

<400> SEQUENCE: 1

Arg Arg Pro Pro Arg
1               5

<210> SEQ ID NO 2
<211> LENGTH: 16
<212> TYPE: PRT
<213> ORGANISM: Rattus norvegicus

<400> SEQUENCE: 2

Arg Gln Ile Lys Ile Trp Phe Gln Asn Arg Met Lys Trp Lys Lys
1               5                   10                  15

<210> SEQ ID NO 3
<211> LENGTH: 178
<212> TYPE: PRT
<213> ORGANISM: Homo sapiens

<400> SEQUENCE: 3

Met Ser Gly Gly Lys Tyr Val Asp Ser Glu Gly His Leu Tyr Thr Val
1               5                   10                  15

Pro Ile Arg Glu Gln Gly Asn Ile Tyr Lys Pro Asn Asn Lys Ala Met
            20                  25                  30

Ala Asp Glu Leu Ser Gly Lys Gln Val Tyr Asp Ala His Thr Lys Glu
        35                  40                  45

Ile Asp Leu Val Asn Arg Asp Pro Lys His Leu Asn Asp Asp Val Val
    50                  55                  60

Lys Ile Asp Phe Glu Asp Val Ile Ala Glu Pro Gly Thr His Ser
65                  70                  75                  80

Phe Asp Gly Ile Trp Lys Ala Ser Phe Thr Thr Phe Thr Val Thr Lys
                85                  90                  95

Tyr Trp Phe Tyr Arg Leu Leu Ser Ala Leu Phe Gly Ile Pro Met Ala
            100                 105                 110

Leu Ile Trp Gly Ile Tyr Phe Ala Ile Leu Ser Phe Leu His Ile Trp
        115                 120                 125

Ala Val Val Pro Cys Ile Lys Ser Phe Leu Ile Glu Ile Gln Cys Ile
    130                 135                 140

Ser Arg Val Tyr Ser Ile Tyr Val His Thr Val Cys Asp Pro Leu Phe
145                 150                 155                 160

Glu Ala Val Gly Lys Ile Phe Ser Asn Val Arg Ile Asn Leu Gln Lys
                165                 170                 175

Glu Ile

<210> SEQ ID NO 4
<211> LENGTH: 151
<212> TYPE: PRT
<213> ORGANISM: Rattus norvegicus

<400> SEQUENCE: 4

Met Met Ala Glu Glu His Thr Asp Leu Glu Ala Gln Ile Val Lys Asp
1               5                   10                  15

Ile His Cys Lys Glu Ile Asp Leu Val Asn Arg Asp Pro Lys Asn Ile
            20                  25                  30
```

```
Asn Glu Asp Ile Val Lys Val Asp Phe Glu Asp Val Ile Ala Glu Pro
         35                  40                  45
Val Gly Thr Tyr Ser Phe Asp Gly Val Trp Lys Val Ser Tyr Thr Thr
 50                  55                  60
Phe Thr Val Ser Lys Tyr Trp Cys Tyr Arg Leu Leu Ser Thr Leu Leu
 65                  70                  75                  80
Gly Val Pro Leu Ala Leu Leu Trp Gly Phe Leu Phe Ala Cys Ile Ser
                 85                  90                  95
Phe Cys His Ile Trp Ala Val Val Pro Cys Ile Lys Ser Tyr Leu Ile
                100                 105                 110
Glu Ile Gln Cys Ile Ser His Ile Tyr Ser Leu Cys Ile Arg Thr Phe
            115                 120                 125
Cys Asn Pro Leu Phe Ala Ala Leu Gly Gln Val Cys Ser Ser Ile Lys
    130                 135                 140
Val Val Leu Arg Lys Glu Val
145                 150
```

<210> SEQ ID NO 5
<211> LENGTH: 20
<212> TYPE: PRT
<213> ORGANISM: Homo sapiens

<400> SEQUENCE: 5

```
Asp Gly Ile Trp Lys Ala Ser Phe Thr Thr Phe Thr Val Thr Lys Tyr
 1               5                  10                  15
Trp Phe Tyr Arg
            20
```

<210> SEQ ID NO 6
<211> LENGTH: 14
<212> TYPE: PRT
<213> ORGANISM: Homo sapiens

<400> SEQUENCE: 6

```
Asp Gly Ile Trp Lys Ala Ser Phe Thr Thr Phe Thr Val Thr
 1               5                  10
```

<210> SEQ ID NO 7
<211> LENGTH: 15
<212> TYPE: DNA
<213> ORGANISM: Artificial
<220> FEATURE:
<223> OTHER INFORMATION: Synthesized

<400> SEQUENCE: 7
cggcgcccgc ctcgt     15

<210> SEQ ID NO 8
<211> LENGTH: 21
<212> TYPE: DNA
<213> ORGANISM: Artificial
<220> FEATURE:
<223> OTHER INFORMATION: Synthesized

<400> SEQUENCE: 8
cggcgcccgc ctcgttgagg g     21

<210> SEQ ID NO 9
<211> LENGTH: 52
<212> TYPE: DNA
<213> ORGANISM: Artificial
<220> FEATURE:

```
<223> OTHER INFORMATION: Synthesized
<220> FEATURE:
<221> NAME/KEY: misc_feature
<222> LOCATION: (11)..(13)
<223> OTHER INFORMATION: n is a, c, g, or t
<220> FEATURE:
<221> NAME/KEY: misc_feature
<222> LOCATION: (15)..(16)
<223> OTHER INFORMATION: n is a, c, g, or t
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t

<400> SEQUENCE: 9
gctagaattc nnnbnnbnnb nnbnnbnnbn nbaagcttac tgcagtagca tg        52

<210> SEQ ID NO 10
<211> LENGTH: 20
<212> TYPE: DNA
<213> ORGANISM: Artificial
<220> FEATURE:
<223> OTHER INFORMATION: Synthesized

<400> SEQUENCE: 10
catgctactg cagtaagctt                                             20

<210> SEQ ID NO 11
<211> LENGTH: 44
<212> TYPE: PRT
<213> ORGANISM: Homo sapiens

<400> SEQUENCE: 11

Lys Ser Phe Leu Ile Glu Ile Gln Cys Thr Ser Arg Val Tyr Ser Ile
1               5                   10                  15

Tyr Val His Thr Val Cys Asp Pro Leu Phe Glu Ala Val Gly Lys Ile
            20                  25                  30

Phe Ser Asn Val Arg Ile Asn Leu Gln Leu Gln Ile
        35                  40

<210> SEQ ID NO 12
<211> LENGTH: 20
<212> TYPE: PRT
<213> ORGANISM: Rattus norvegicus

<400> SEQUENCE: 12

Asp Glu Val Trp Arg Val Ser Tyr Thr Thr Phe Thr Val Thr Lys Tyr
1               5                   10                  15

Trp Cys Tyr Arg
            20

<210> SEQ ID NO 13
```

```
<211> LENGTH: 22
<212> TYPE: PRT
<213> ORGANISM: Rattus norvegicus

<400> SEQUENCE: 13

Lys Ser Tyr Leu Ile Glu Ile Gln Cys Ile Ser His Ile Tyr Ser Leu
1               5                   10                  15

Cys Ile Arg Thr Phe Cys
            20

<210> SEQ ID NO 14
<211> LENGTH: 13
<212> TYPE: PRT
<213> ORGANISM: Homo sapiens

<400> SEQUENCE: 14

Phe Thr Thr Phe Thr Val Thr Lys Tyr Trp Phe Tyr Arg
1               5                   10

<210> SEQ ID NO 15
<211> LENGTH: 7
<212> TYPE: PRT
<213> ORGANISM: Homo sapiens

<400> SEQUENCE: 15

Phe Thr Thr Phe Thr Val Thr
1               5

<210> SEQ ID NO 16
<211> LENGTH: 7
<212> TYPE: PRT
<213> ORGANISM: Homo sapiens

<400> SEQUENCE: 16

Ala Thr Thr Phe Thr Val Thr
1               5

<210> SEQ ID NO 17
<211> LENGTH: 7
<212> TYPE: PRT
<213> ORGANISM: Homo sapiens

<400> SEQUENCE: 17

Phe Thr Thr Phe Ala Val Thr
1               5

<210> SEQ ID NO 18
<211> LENGTH: 7
<212> TYPE: PRT
<213> ORGANISM: Homo sapiens

<400> SEQUENCE: 18

Phe Thr Thr Phe Thr Ala Thr
1               5

<210> SEQ ID NO 19
<211> LENGTH: 7
<212> TYPE: PRT
<213> ORGANISM: Homo sapiens

<400> SEQUENCE: 19

Phe Thr Thr Phe Thr Val Ala
1               5
```

```
<210> SEQ ID NO 20
<211> LENGTH: 20
<212> TYPE: PRT
<213> ORGANISM: Artificial
<220> FEATURE:
<223> OTHER INFORMATION: Synthesized

<400> SEQUENCE: 20

Trp Gly Ile Asp Lys Ala Phe Phe Thr Thr Ser Thr Val Thr Tyr Lys
1               5                   10                  15

Trp Phe Arg Tyr
        20

<210> SEQ ID NO 21
<211> LENGTH: 16
<212> TYPE: PRT
<213> ORGANISM: Drosophila melanogaster

<400> SEQUENCE: 21

Arg Gln Ile Lys Ile Trp Phe Gln Asn Arg Arg Met Lys Trp Lys Lys
1               5                   10                  15

<210> SEQ ID NO 22
<211> LENGTH: 36
<212> TYPE: PRT
<213> ORGANISM: Artificial
<220> FEATURE:
<223> OTHER INFORMATION: Drosophila melanogaster

<400> SEQUENCE: 22

Arg Gln Ile Lys Ile Trp Phe Gln Asn Arg Arg Met Lys Trp Lys Lys
1               5                   10                  15

Asp Gly Ile Trp Lys Ala Ser Phe Thr Thr Phe Thr Val Thr Lys Tyr
            20                  25                  30

Trp Phe Tyr Arg
        35

<210> SEQ ID NO 23
<211> LENGTH: 36
<212> TYPE: PRT
<213> ORGANISM: Artificial
<220> FEATURE:
<223> OTHER INFORMATION: Drosophila melanogaster

<400> SEQUENCE: 23

Arg Gln Ile Lys Ile Trp Phe Gln Asn Arg Arg Met Lys Trp Lys Lys
1               5                   10                  15

Trp Gly Ile Asp Lys Ala Phe Phe Thr Thr Ser Thr Val Thr Tyr Lys
            20                  25                  30

Trp Phe Arg Tyr
        35
```

UNITED STATES PATENT AND TRADEMARK OFFICE
CERTIFICATE OF CORRECTION

PATENT NO. : 10,537,607 B2
APPLICATION NO. : 15/039826
DATED : January 21, 2020
INVENTOR(S) : David Eveleth and William C. Sessa Page 1 of 1

It is certified that error appears in the above-identified patent and that said Letters Patent is hereby corrected as shown below:

In the Specification

Column 1, Line 9 add:
STATEMENT REGARDING FEDERALLY SPONSORED RESEARCH OR DEVELOPMENT
This invention was made with government support under HL096670, HL081190, HL064793 and HL061371 awarded by National Institutes of Health. The government has certain rights in the invention.

Signed and Sealed this
Seventeenth Day of December, 2024

Derrick Brent
*Acting Director of the United States Patent and Trademark Office*